United States Patent
Hilbert et al.

(10) Patent No.: US 9,593,384 B2
(45) Date of Patent: Mar. 14, 2017

(54) METRONIDAZOLE RESISTANCE IN TRICHOMONAS VAGINALIS AND SINGLE NUCLEOTIDE POLYMORPHISMS

(71) Applicants: David W Hilbert, Burlington, NJ (US); Scott E Gygax, Yardley, PA (US); Martin E. Adelson, East Windsor, NJ (US); Eli Mordechai, Robbinsville, NJ (US); Jessica Schuyler, Burlington, NJ (US); Teresa Paulish-Miller, Yardley, PA (US)

(72) Inventors: David W Hilbert, Burlington, NJ (US); Scott E Gygax, Yardley, PA (US); Martin E. Adelson, East Windsor, NJ (US); Eli Mordechai, Robbinsville, NJ (US); Jessica Schuyler, Burlington, NJ (US); Teresa Paulish-Miller, Yardley, PA (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 138 days.

(21) Appl. No.: 14/258,339

(22) Filed: Apr. 22, 2014

(65) Prior Publication Data

US 2014/0377749 A1 Dec. 25, 2014

Related U.S. Application Data

(62) Division of application No. 13/680,553, filed on Nov. 19, 2012, now Pat. No. 8,741,563.

(60) Provisional application No. 61/629,661, filed on Nov. 23, 2011.

(51) Int. Cl.
*C07H 21/04* (2006.01)
*C12P 19/34* (2006.01)
*C12Q 1/68* (2006.01)

(52) U.S. Cl.
CPC .......... *C12Q 1/6895* (2013.01); *C12Q 1/689* (2013.01); *C12Q 1/6869* (2013.01); *C12Q 2600/156* (2013.01)

(58) Field of Classification Search
None
See application file for complete search history.

(56) References Cited

U.S. PATENT DOCUMENTS 5,474,796 A * 12/1995 Brennan .............. B01J 19/0046
422/547

OTHER PUBLICATIONS

Hexanucleotide mix (Boehringer-Mannheim Biochemical catalog, 1997, pp. 95).*

\* cited by examiner

*Primary Examiner* — Sarae Bausch
(74) *Attorney, Agent, or Firm* — Siu K. Lo

(57) ABSTRACT

The present invention is directed to the discovery of single nucleotide polymorphisms (SNPs) in the presence of metronidazole-resistant *Trichomonas vaginalis*. The presence of G76C, C213G, or C318A (SNP) in tvntr 4 or the presence of A238T, G427C, or T476C (SNP) in tvntr6 provides a reliable biomarker for the presence of metronidazole-resistant *Trichomonas vaginalis*. The present invention further provides reagents used for detecting the SNPs to screen subjects for metronidazole resistance in *Trichomonas vaginalis*.

7 Claims, 9 Drawing Sheets

Figure 1   Nucleotide Sequence Alignment of *tvntr4* Gene from Metronidazole-
Susceptible (G3) and –Resistant (42701) *Trichomonas vaginalis*

```
CLUSTAL 2.1 multiple sequence alignment

G3          ATGAGTGTCCTTAAGTGCATCCAAGCTAGAAGAACAATTAGACACTATGTTCAGGGCGAA  60
42701       ------------------------------------------------------------

G76C
G3          GAAGTTCCAAAGGCAG ATATTGATCTCATCGCAAACAGTGGCTTAACTGCTCCATCTTCT 120
42701       -AAGTTCCAAAGGCAC ATATTGATCTCATCGCAAACAGTGGCTTAACTGCTCCATCTTCT  59
             ************** ********************************************

G3          ATGGATATCCAAGGTGTCGACATCTACGTCGTCAGAGGCCAAGAAAAGCTTGCCAAGATT 180
42701       ATGGATATCCAAGGTGTCGACATCTACGTCGTCAGAGGCCAAGAAAAGCTTGCCAAGATT 119
            ************************************************************
                                              C213G
G3          GAAGAAGCTACACTCAAGGCCCTTCCAGAATA C CCACAAAGTACTTCGTTAATCGTCAT 240
42701       GAAGAAGCTACACTCAAGGCCCTTCCAGAATA G CCACAAAGTACTTCGTTAATCGTCAT 179
            ******************************** *************************

G3          GAACAGCTTCATGTTAAGAACGTTATCACCTGCGATGCTCCAGTTCTTTTCGTCTTAGTT 300
42701       GAACAGCTTCATGTTAAGAACGTTATCACCTGCGATGCTCCAGTTCTTTTCGTCTTAGTT 239
            ************************************************************
                              C318A
G3          AAGAATGAGAGAGCTCA C AAGATTACTATCATATCGATTGCGGTCTCATCGTCGAATCA 360
42701       AAGAATGAGAGAGCTCA A AAGATTACTATCATATCGATTGCGGTCTCATCGTCGAATCA 299
            ***************** ******************************************

G3          ATGATTTTGCTTGCCCAAGATATGGGATACAGCACAATGTGCATCGGTGCTATCGGTATG 420
42701       ATGATTTTGCTTGCCCAAGATATGGGATACAGCACAATGTGCATCGGTGCTATCGGTATG 359
            ************************************************************

G3          GCTGATCTTTCTGAAGTTCTTGGTATTCCAAAGGATGCTGCTATTATGGGTCTTGCCATG 480
42701       GCTGATCTTTCTGAAGTTCTTGGTATTCCAAAGGATGCTGCTATTATGGGTCTTGCCATG 419
            ************************************************************

G3          GGTAAAGCTGCCCCAGAACAGGATCTTCATAAAAGGCCAATCAAGTCTAAGGTAGTTTAT 540
42701       GGTAAAGCTGCCCCAGAACAGGATCTTCATAAAAGGCCAATCAAGTCTAAGGTAGTT--- 476
            ********************************************************

G3          GCTGACTAA 549  SEQ ID NO: 12
42701       ---------       SEQ ID NO: 13
```

Figure 2 Amino Acid Sequence Alignment of Tvntr4 Protein from Metronidazole-Susceptible (G3) and –Resistant (42701) *Trichomonas vaginalis*

```
GENE ID: 4752720 TVAG_205740 | nitroreductase family protein
[Trichomonas vaginalis G3] (10 or fewer PubMed links)

Score =  309 bits (777),  Expect = 9e-105
Identities = 155/158 (98%), Positives = 155/158 (98%), Gaps = 0/158 (0%)
Frame = +3
                  D26H                                         Y71STOP
Query   3    VPKAHDLIANSGLTAPSSMDIQGVDIYVVRGQEKLAKIEEATLKALPE*ATKYFWRHE   182
             VPKA DLIANSGLTAPSSMDIQGVDIYVVRGQEKLAKIEEATLKALPE ATKYFWRHE
Sbjct   22   VPKADDLIANSGLTAPSSMDIQGVDIYVVRGQEKLAKIEEATLKALPEYATKYFWRHE    81
                                              H106O
Query   183  QLHVKNVITCDAPVLFVLVKNERAGKDYYHIDCGLIVESMILLAQDMGYSTMCIGAIGMA  362
             QLHVKNVITCDAPVLFVLVKNERA  DYYHIDCGLIVESMILLAQDMGYSTMCIGAIGMA
Sbjct   82   QLHVKNVITCDAPVLFVLVKNERAHHDYYHIDCGLIVESMILLAQDMGYSTMCIGAIGMA  141

Query   363  DLSEVLGIPKDAAIMGLAMGKAAPEQDLHKRPIKSKVV   476   SEQ ID NO 14
             DLSEVLGIPKDAAIMGLAMGKAAPEQDLHKRPIKSKVV         SEQ ID NO 20
Sbjct   142  DLSEVLGIPKDAAIMGLAMGKAAPEQDLHKRPIKSKVV   179   SEQ ID NO 15
```

Figure 3  Alignment of Primers for PCR Amplification and Sequencing of
*tvntr4* Gene from Metronidazole-Susceptible (G3) and –Resistant
(42701) *Trichomonas vaginalis*

```
CLUSTAL 2.1 multiple sequence alignment
                       SEQ ID NO 1
G3         ATGAGTGTCCTTAAGTGCATCCAAGCTAGAAGAACAATTAGACACTATGTTCAGGGCGAA  60
42701      ------------------------------------------------------------

G76C
G3         GAAGTTCCAAAGGCAGATATTGATCTCATCGCAAACAGTGGCTTAACTGCTCCATCTTCT  120
42701       -AAGTTCCAAAGGCACATATTGATCTCATCGCAAACAGTGGCTTAACTGCTCCATCTTCT  59
            ************** *********************************************

G3         ATGGATATCCAAGGTGTCGACATCTACGTCGTCAGAGGCCAAGAAAAGCTTGCCAAGATT  180
42701      ATGGATATCCAAGGTGTCGACATCTACGTCGTCAGAGGCCAAGAAAAGCTTGCCAAGATT  119
           ************************************************************

C213G
G3         GAAGAAGCTACACTCAAGGCCCTTCCAGAATCCCACAAAGTACTTCGTTAATCGTCAT  240
42701      GAAGAAGCTACACTCAAGGCCCTTCCAGAATGCCCACAAAGTACTTCGTTAATCGTCAT  179
           ******************************  ****************************

G3         GAACAGCTTCATGTTAAGAACGTTATCACCTGCGATGCTCCAGTTCTTTCGTCTTAGTT  300
42701      GAACAGCTTCATGTTAAGAACGTTATCACCTGCGATGCTCCAGTTCTTTCGTCTTAGTT  239
           ************************************************************

C318A
G3         AAGAATGAGAGAGCTCACAAGATTACTATCATATCGATTGCGGTCTCATCGTCGAATCA  360
42701      AAGAATGAGAGAGCTCAAAAGATTACTATCATATCGATTGCGGTCTCATCGTCGAATCA  299
           *****************  *****************************************

G3         ATGATTTTGCTTGCCCAAGATATGGGATACAGCACAATGTGCATCGGTGCTATCGGTATG  420
42701      ATGATTTTGCTTGCCCAAGATATGGGATACAGCACAATGTGCATCGGTGCTATCGGTATG  359
           ************************************************************

G3         GCTGATCTTTCTGAAGTTCTTGGTATTCCAAAGGATGCTGCTATTATGGGTCTTGCCATG  480
42701      GCTGATCTTTCTGAAGTTCTTGGTATTCCAAAGGATGCTGCTATTATGGGTCTTGCCATG  419
           ************************************************************
                                                              SEQ ID NO 2
G3         GGTAAAGCTGCCCCAGAACAGGATCTTCATAAAAGGCCAATCAAGTCTAAGGTAGTTTAT  540
42701      GGTAAAGCTGCCCCAGAACAGGATCTTCATAAAAGGCCAATCAAGTCTAAGGTAGTT---  476
           ******************************************************
           SEQ ID NO 2
G3         GCCGACTAA  549   SEQ ID NO: 12
42701      ---------        SEQ ID NO: 13
```

Figure 4    Nucleotide Sequence Alignment of *tvntr6* Gene from Metronidazole-Susceptible (G3) and –Resistant (50141) *Trichomonas vaginalis*

```
CLUSTAL 2.1 multiple sequence alignment

G3          CATTGAATTTATTCGTTCAAAATTTATTGCCTGCCGAATATCTCCGCAAAATGAAGAAGA  60
50141       ------------------------------------------------------------

G3          AGGCAATATATGTTTATGATAAAAATTGGGGATAAATTTTTTGATAGTAGCCTTTCAAAT 120
50141       AGGCAATATATTTTTATGATAAAAATTGGGGATAAATTTTTTGATAGTAGCCTTTCAAAT  60
            *********** ************************************************

G3          TTTTGTAAGAAAATTTTGGAGAAACTGTTCGGAAAACTAATTGAAAAGAAAAATCTCAAA 180
50141       TTTTGTAAGAAAATTTTGGAGAAACTGTTCGGAAAACTAATTGAAAAGAAAAATCTCAAA 120
            ************************************************************

G3          TATGACTTCATTTTTAGATAATGTCTATCTCACAACTCAAGTCCAGACGCACAATCAGAT 240
50141       TATGACTTCATTTTTAGATAATGTCTATCTCACAACTCAAGTCCAGACGCACAATCAGAT 180
            ************************************************************

G3          GCTATGATCCAAACTATGTCATTCCAAAGGAAGACTTAGAGAAAATTGTTGATGCAGCTT 300
50141       GCTATGATCCAAACTATGTCATTCCAAAGGAAGACTTAGAGAAAATTGTTGATGCAGCTT 240
            ************************************************************

G3          TCAACTCTCCATCAGCTATGAATGTTCAGGAAACAGATCTCGTCGTTGTTACAAACAAGG 360
50141       TCAACTCTCCATCAGCTATGAATGTTCAGGAAACAGATCTCGTCGTTGTTACAAACAAGG 300
            ************************************************************

G3          AAAAACTCCAAAAGCTTAACGATGCTGTTTTTGCTTCCCTTGATGAGAAGTCTCAACAAA 420
50141       AAAAACTCCAAAAGCTTAACGATGCTGTTTTTGCTTCCCTTGATGAGAAGTCTCAACAAA 360
            ************************************************************
                                       A238T
G3          TGTACCTTGGAATGCAAAAGCAGACACATGTTAAGCAGGAAGTTCTCTATGATTGCTCTG 480
50141       TGTACCTTGGAATGCAATTAGCAGACACATGTTAAGCAGGAAGTTCTCTATGATTGCTCTG 420
            *****************  *****************************************

G3          CTGTTTTCCTTCTTGTCAAGAATGAGCGTGCATCCCCAGCCATTCAACAACTTGATTCCG 540
50141       CTGTTTTCCTTCTTGTCAAGAATGAGCGTGCATCCCCAGCCATTCAACAACTTGATTCCG 480
            ************************************************************

G3          GTATTCTCGCCATGAGTGTTTTGATGGCTGCCCATGATCTTGGACTTGGTACGGTTCCTC 600
50141       GTATTCTCGCCATGAGTGTTTTGATGGCTGCCCATGATCTTGGACTTGGTACAGTTCCTC 540
            **************************************************** ******
                                       G427C
G3          TTGGTACACTTATCCGCCCACAAACGGAGAAGTTCTTGGTCTTCCACCAAAATCAGTTC 660
50141       TTGGTACACTTATCCGCCCACAAACCGAGAAGTTCTTGGTCTTCCACCAAAATCAGTTC 600
            ************************* **********************************
            T476C
G3          TTCTTGGCATTGGTGTTGGCAAACCATTATCTTTCGAGCCTCATCCAAAGGAAAACCTTA 720
50141       TTCTTGGCATTGGTGCTGGCAAACCATTATCTTTCGAGCCTCATCCAAAGGAAAACCTTA 660
            *************** ********************************************

G3          GAAAGGTTACATACATTGAATAA 743        SEQ ID NO: 16
50141       GAAAGGTTA--------------- 669       SEQ ID NO: 17
            *********
```

Figure 5    Amino Acid Sequence Alignment of Tvntr6 Protein from
            Metronidazole-Susceptible (G3) and –Resistant (50141) *Trichomonas
            vaginalis*

```
GENE ID: 4753551 TVAG_354010 | nitroreductase family protein
(Trichomonas vaginalis G3) (10 or fewer PubMed links)

Score =  340 bits (873),  Expect = 2e-118
 Identities = 174/177 (98%), Positives = 175/177 (99%), Gaps = 0/177 (0%)
 Frame = +1

Query     133  MSISQLKSRRTIRCYDPNYVIPKEDLEKIVDAAFNSPSAMSVQETDLVVVTNKEKLQKLN  312
Consensus      MSISQLKSRRTIRCYDPNYVIPKEDLEKIVDAAFNSPSAMSVQETDLVVVTNKEKLQKLN
Sbjct       1  MSISQLKSRRTIRCYDPNYVIPKEDLEKIVDAAFNSPSAMSVQETDLVVVTNKEKLQKLN   60
                                                  K80STOP
Query     313  DAVFRSLDEKSQQMYLGKQ*ITHVKQEVLYDCSAVFLLVKNERASPAIQQLDSGILAMSV  492
Consensus      DAVFRSLDEKSQQMYLGK   THVKQEVLYDCSAVFLLVKNERASPAIQQLDSGILAMSV
Sbjct      61  DAVFRSLDEKSQQMYLGKKITHVKQEVLYDCSAVFLLVKNERASPAIQQLDSGILAMSV  120
                                    E143Q         V159A
Query     493  LMAAHDLGLGTVPLGTLIRPQEQIVLGLPPKSVLLGISAKKPLSFEPHPKENLRKVT    663
Consensus      LMAAHDLGLGTVPLGTLIRPQT+ VLGLPPKSVLLGIS +KPLSFEPHPKENLRKVT
Sbjct     121  LMAAHDLGLGTVPLGTLIRPQTE VLGLPPKSVLLGIGV KPLSFEPHPKENLRKVT    177
```

Query = SEQ ID NO 18

Consensus = SEQ ID NO 21

Subject = SEQ ID NO 19

Figure 6  Alignment of Primers for PCR Amplification and Sequencing of *tvntr6* Gene A238T, G427C and T476C SNPs from Metronidazole-Susceptible (G3) and –Resistant (50141) *Trichomonas vaginalis*

```
CLUSTAL 2.1 multiple sequence alignment
                    SEQ ID NO 3
G3      CATTGAATTTATTCGTTCAAAATTTATTGCCTGCCAATATCTCCGCAAAATGAAGAAGA  60
50141   ------------------------------------------------------------

G3      AGGCAATATATGTTTATGATAAAAATTGGGGATAAATTTTTGATAGTAGCCTTTCAAAT  120
50141   AGGCAATATATTTTTATGATAAAAATTGGGGATAAATTTTTGATAGTAGCCTTTCAAAT  60
        ********** * ***********************************************

G3      TTTTGTAAGAAAATTTTGGAGAAACTGTTCGGAAAACTAATTGAAAAGAAAAATCTCAAA  180
50141   TTTTGTAAGAAAATTTTGGAGAAACTGTTCGGAAAACTAATTGAAAAGAAAAATCTCAAA  120
        ************************************************************

G3      TATGACTTCATTTTTAGATAATGTCTATCTCACACTCAAGTCCAGACGCACAATCAGAT  240
50141   TATGACTTCATTTTTAGATAATGTCTATCTCACACTCAAGTCCAGACGCACAATCAGAT  180
        ************************************************************

G3      GCTATGATCCAAACTATGTCATTCCAAAGGAAGACTTAGAGAAAATTGTTGATGCAGCTT  300
50141   GCTATGATCCAAACTATGTCATTCCAAAGGAAGACTTAGAGAAAATTGTTGATGCAGCTT  240
        ************************************************************

G3      TCAACTCTCCATCAGCTATGAATGTTCAGGAAACAGATCTCGTCGTTGTTACAAACAAGG  360
50141   TCAACTCTCCATCAGCTATGAATGTTCAGGAAACAGATCTCGTCGTTGTTACAAACAAGG  300
        ************************************************************

G3      AAAAACTCCAAAAGCTTAACGATGCTGTTTTTGCTTCCCTTGATGAGAAGTCTCAACAAA  420
50141   AAAAACTCCAAAAGCTTAACGATGCTGTTTTTGCTTCCCTTGATGAGAAGTCTCAACAAA  360
        ************************************************************
                              A238T
G3      TGTACCTTGGAATGCAAAGCAGACACATGTTAAGCAGGAAGTTCTCTATGATTGCTCTG  480
50141   TGTACCTTGGAATGCAATAGCAGACACATGTTAAGCAGGAAGTTCTCTATGATTGCTCTG  420
        ***************** ******************************************

G3      CTGTTTTCCTTCTTGTCAAGAATGAGCGTGCATCCCCAGCCATTCAACAACTTGATTCCG  540
50141   CTGTTTTCCTTCTTGTCAAGAATGAGCGTGCATCCCCAGCCATTCAACAACTTGATTCCG  480
        ************************************************************

G3      GTATTCTCGCCATGAGTGTTTTGATGGCTGCCCATGATCTTGGACTTGGTACGGTTCCTC  600
50141   GTATTCTCGCCATGAGTGTTTTGATGGCTGCCCATGATCTTGGACTTGGTACAGTTCCTC  540
        **************************************************** ******
                                          G427C
G3      TTGGTACACTTATCCGCCCACAAACAGAGAAGTTCTTGGTCTTCCACCAAAATCAGTTC  660
50141   TTGGTACACTTATCCGCCCACAAACACAGAAGTTCTTGGTCTTCCACCAAAATCAGTTC  600
        ************************* **********************************
              T476C
G3      TTCTTGGCATTGGTTTGGCAAACCATTATCTTTCGAGCCTCATCCAAAGGAAAACCTTA  720
50141   TTCTTGGCATTGGTCTGGCAAACCATTATCTTTCGAGCCTCATCCAAAGGAAAACCTTA  660
        ************** *********************************************
              SEQ ID NO 4
G3      GAAAGGTTACATACATTGAATAA   743   SEQ ID NO: 16
50141   GAAAGGTTA--------------   669   SEQ ID NO: 17
        *********
```

Figure 7   Alignment of Primers and Probes for Real-Time PCR Detection of
            tvntr6 Gene A238T SNP from Metronidazole-Susceptible (G3) and –
            Resistant (50141) Trichomonas vaginalis

```
CLUSTAL 2.1 multiple sequence alignment

G3         CATTGAATTTATTCGTTCAAAATTTATTGCCTGCCGAATATCTCCGCAAAATGAAGAAGA  60
50141      ------------------------------------------------------------

G3         AGGCAATATATGTTTATGATAAAAATTGGGGATAAATTTTTTGATAGTAGCCTTTCAAAT 120
50141      AGGCAATATATTTTTATGATAAAAATTGGGGATAAATTTTTTGATAGTAGCCTTTCAAAT  60
           *********** ************************************************

G3         TTTTGTAAGAAAATTTTGGAGAAACTGTTCGGAAAACTAATTGAAAAGAAAAATCTCAAA 180
50141      TTTTGTAAGAAAATTTTGGAGAAACTGTTCGGAAAACTAATTGAAAAGAAAAATCTCAAA 120
           ************************************************************

G3         TATGACTTCATTTTTAGATAATGTCTATCTCACAACTCAAGTCCAGACGCACAATCAGAT 240
50141      TATGACTTCATTTTTAGATAATGTCTATCTCACAACTCAAGTCCAGACGCACAATCAGAT 180
           ************************************************************

G3         GCTATGATCCAAACTATGTCATTCCAAAGGAAGACTTAGAGAAAATTGTTGATGCAGCTT 300
50141      GCTATGATCCAAACTATGTCATTCCAAAGGAAGACTTAGAGAAAATTGTTGATGCAGCTT 240
           ************************************************************
                               SEQ ID NO 5
G3         TCAACTCTCCATCAGCTATGAATGTTCAGGAAACAGATCTCGTCGTTGTTACAAACAAGG 360
50141      TCAACTCTCCATCAGCTATGAATGTTCAGGAAACAGATCTCGTCGTTGTTACAAACAAGG 300
           ************************************************************

G3         AAAAACTCCAAAAGCTTAACGATGCTGTTTTTGCTTCCCTTGATGAGAAGTCTCAACAAA 420
50141      AAAAACTCCAAAAGCTTAACGATGCTGTTTTTGCTTCCCTTGATGAGAAGTCTCAACAAA 360
           ************************************************************
                        SEQ ID NO 7
G3         TGTACCTTGGAATGCAAAAGCAGACACATGTTAAGCAGGAAGTTCTCTATGATTGCTCTG 480
50141      TGTACCTTGGAATGCAATAGCAGACACATGTTAAGCAGGAAGTTCTCTATGATTGCTCTG 420
           ***************** ******************************************
              SEQ ID NO 8                       SEQ ID NO 6
G3         CTGTTTTCCTTCTTGTCAAGAATGAGCGTGCATCCCAGCCATTCAACAACTTGATTCCG 540
50141      CTGTTTTCCTTCTTGTCAAGAATGAGCGTGCATCCCAGCCATTCAACAACTTGATTCCG 480
           ************************************************************

G3         GTATTCTCGCCATGAGTGTTTTGATGGCTGCCCATGATCTTGGACTTGGTACGGTTCCTC 600
50141      GTATTCTCGCCATGAGTGTTTTGATGGCTGCCCATGATCTTGGACTTGGTACAGTTCCTC 540
           **************************************************** ******

G3         TTGGTACACTTATCCGCCCACAAACAGAAGAAGTTCTTGGTCTTCCACCAAAATCAGTTC 660
50141      TTGGTACACTTATCCGCCCACAAACACAAGAAGTTCTTGGTCTTCCACCAAAATCAGTTC 600
           ************************** *********************************

G3         TTCTTGGCATTGGTGTTGGCAAACCATTATCTTTCGAGCCTCATCCAAAGGAAAACCTTA 720
50141      TTCTTGGCATTGGTGCTGGCAAACCATTATCTTTCGAGCCTCATCCAAAGGAAAACCTTA 660
           *************** ********************************************

G3         GAAAGGTTACATACATTGAATAA 743    SEQ ID NO: 16
50141      GAAAGGTTA-------------- 669    SEQ ID NO: 17
           *********
```

Figure 8   Real-Time PCR Amplification Plots in the Detection of the *tvntr6* Gene A238T SNP
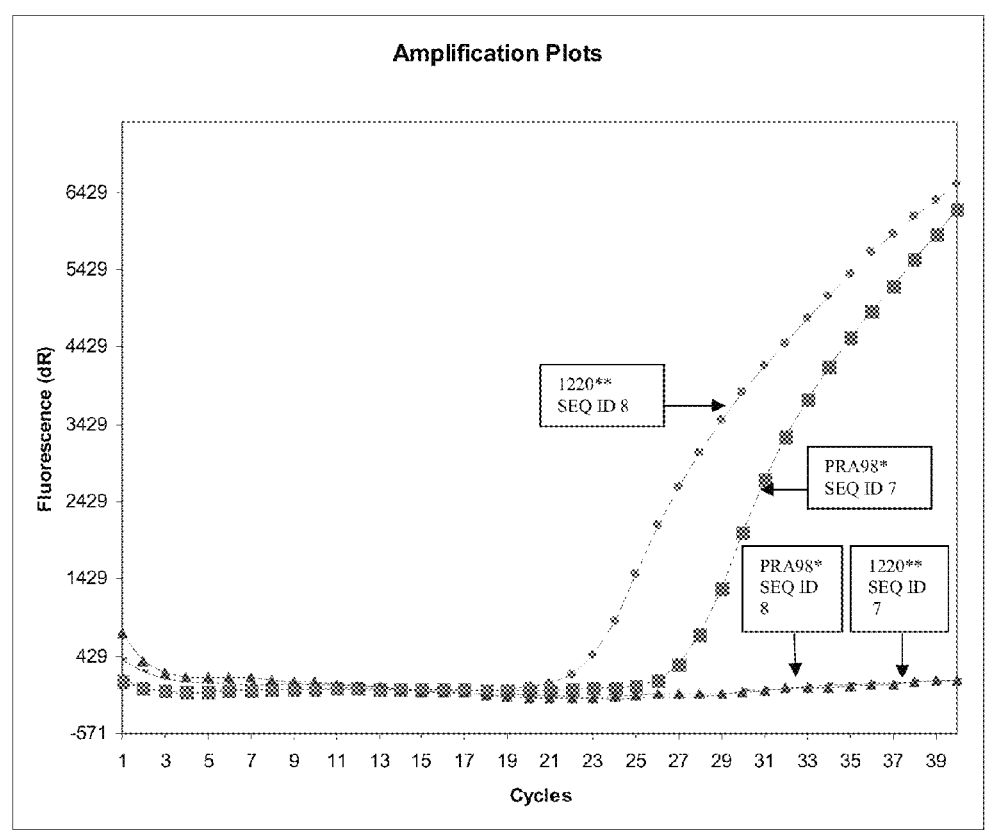
*PRA98 is a metronidazole-susceptible *Trichomonas vaginalis* isolate.
**1220 is a metronidazole-resistant *Trichomonas vaginalis* isolate Figure 9    Alignment of Primers and Probes for Alternate Method of Real-Time
            PCR Detection of *tvntr6* Gene A238T SNP from Metronidazole-
            Susceptible (G3) and –Resistant (50141) *Trichomonas vaginalis*

```
CLUSTAL 2.1 multiple sequence alignment

G3        CATGAATTTATTCGTTCAAAATTTATTGCCTGCCGAATATCTCCGCAAAATGAAGAAGA  60
50141     ------------------------------------------------------------

G3        AGGCAATATATGTTTATGATAAAAATTGGGGATAAAATTTTTGATAGTAGCCTTTCAAAT 120
50141     AGGCAATATATTTTTATGATAAAAATTGGGGATAAAATTTTTGATAGTAGCCTTTCAAAT  60
          ********** * ***********************************************

G3        TTTTGTAAGAAAATTTTGGAGAAACTGTTCGGAAAACTAATTGAAAAGAAAAATCTCAAA 180
50141     TTTTGTAAGAAAATTTTGGAGAAACTGTTCGGAAAACTAATTGAAAAGAAAAATCTCAAA 120
          ************************************************************

G3        TATGACTTCATTTTTAGATAATGTCTATCTCACAACTCAAGTCCAGACGCACAATCAGAT 240
50141     TATGACTTCATTTTTAGATAATGTCTATCTCACAACTCAAGTCCAGACGCACAATCAGAT 180
          ************************************************************

G3        GCTATGATCCAAAACTATGTCATTCCAAAGGAAGACTTAGAGAAAATTGTTGATGCAGCTT 300
50141     GCTATGATCCAAAACTATGTCATTCCAAAGGAAGACTTAGAGAAAATTGTTGATGCAGCTT 240
          ************************************************************
                                                        SEQ ID NO 9
                                                        ──────────▶
G3        TCAACTCTCCATCAGCTATGAATGTTCAGGAAACAGATCTCGTCGTTGTTACAAACAAGG 360
50141     TCAACTCTCCATCAGCTATGAATGTTCAGGAAACAGATCTCGTCGTTGTTACAAACAAGG 300
          ************************************************************
          SEQ ID NO 9
          ──────────▶
G3        AAAAACTCCAAAAGCTTAACGATGCTGTTTTTGCTTCCCTTGATGAGAAGTCTCAACAAA 420
50141     AAAAACTCCAAAAGCTTAACGATGCTGTTTTTGCTTCCCTTGATGAGAAGTCTCAACAAA 360
          ************************************************************
                SEQ ID NO 11
                ──────────▶
G3        TGTACCTTGGAATGCAAAAGCAGACACATGTTAAGCAGGAAGTTCTCTATGATTGCTCTG 480
50141     TGTACCTTGGAATGCAATAGCAGACACATGTTAAGCAGGAAGTTCTCTATGATTGCTCTG 420
          ***************** ******************************************

G3        CTGTTTTCCTTCTTGTCAAGAATGAGCGTGCATCCCAGCCATTCAACAACTTGATTCCG 540
50141     CTGTTTTCCTTCTTGTCAAGAATGAGCGTGCATCCCAGCCATTCAACAACTTGATTCCG 480
          ************************************************************
                          ◀──────────
                          SEQ ID NO 10
G3        GTATTCTCGCCATGAGTGTTTTGATGGCTGCCCATGATCTTGGACTTGGTACGGTTCCTC 600
50141     GTATTCTCGCCATGAGTGTTTTGATGGCTGCCCATGATCTTGGACTTGGTACAGTTCCTC 540
          **************************************************** ******

G3        TTGGTACACTTATCCGCCCACAAACAGAAGAAGTTCTTGGTCTTCCACCAAAATCAGTTC 660
50141     TTGGTACACTTATCCGCCCACAAACACAAGAAGTTCTTGGTCTTCCACCAAAATCAGTTC 600
          ************************** *********************************

G3        TTCTTGGCATTGGTGTTGGCAAACCATTATCTTTCGAGCCTCATCCAAAGGAAACCTTA 720
50141     TTCTTGGCATTGGTGCTGGCAAACCATTATCTTTCGAGCCTCATCCAAAGGAAACCTTA 660
          *************** *********************************************

G3        GAAAGGTTACATACATTGAATAA  743   SEQ ID NO: 16
50141     GAAAGGTTA--------------  669   SEQ ID NO: 17
          *********
```

US 9,593,384 B2

METRONIDAZOLE RESISTANCE IN TRICHOMONAS VAGINALIS AND SINGLE NUCLEOTIDE POLYMORPHISMS

CROSS-REFERENCE TO RELATED APPLICATION

This application is a divisional of U.S. application Ser. No. 13/680,553 filed Nov. 19, 2012, which claims the benefit under 35 U.S.C. §119(e) to U.S. Provisional Application No. 61/629,661 filed Nov. 23, 2011, the content of which is incorporated by reference herein in its entirety.

FIELD OF THE INVENTION

The present invention generally relates to the field of diagnosis of *Trichomonas vaginalis* that exhibits antibiotic resistance. Specifically, the present invention provides previously unrecognized single nucleotide polymorphisms (SNPs) present in metronidazole-resistant *Trichomonas vaginalis*. The identified novel SNPs are present in two (2) nitroreductase genes (tvntr) (i.e., tvntr4 and tvntr6) and useful for screening *Trichomonas vaginalis* that exhibit metronidazole resistance. Methods and reagents for detecting the presence of these novel gene polymorphisms are also provided.

BACKGROUND OF THE INVENTION

*Trichomonas vaginalis* is an anaerobic, flagellated haploid protozoan. *Trichomonas vaginalis* is sexually transmitted in humans, causing >7 million infections annually in the United States. Infection with *Trichomonas vaginalis* (i.e., trichomoniasis) is a common cause of vaginitis, and is associated with HIV transmission and obstetric complications. Patients suffering from *Trichomonas vaginalis* are normally treated with antibiotics such as metronidazole. Metronidazole is a pro-drug believed to undergo reduction to a nitro radical anion form by anaerobic metabolism. The anion form of metronidazole is thought to kill the microorganisms by non-specifically damaging proteins and DNA in *Trichomonas vaginalis*.

Despite that metronidazole treatment is reported to be 85-95% effective, there is an estimated 2.5%-10% clinical isolates of *Trichomonas vaginalis* that exhibit varying degrees of metronidazole resistance. Given the significant occurrence of trichomoniasis, emerging metronidazole resistance in *Trichomonas vaginalis* is posing a significant problem to public health.

It is suggested that metronidazole resistance in vitro may result in loss of hydrogenosome enzymes such as hydrogenase, ferredoxin and pyruvate:ferredoxin oxidoreductase. These enzymes are thought to play a role in reducing metronidazole to its active form. The cytoplasmic enzyme thioredoxin reductase may similarly contribute in metronidazole resistance.

Current methodology for detecting metronidazole resistance in *Trichomonas vaginalis* requires culturing the microorganism in a laboratory under serial dilutions of antibiotic (e.g., metronidazole) to determine the minimum lethal concentration. This culturing methodology suffers many problems: (a) it requires a viable *Trichomonas vaginalis* culture derived from a patient; (b) it requires highly trained personnel; and (c) it is time-consuming and often requires weeks to obtain results.

Accordingly, there is a continuing need for an improved method that allows rapid and reliable detection of metronidazole resistance in *Trichomonas vaginalis* without culturing. The present inventors resolved all the prior art deficiency and discovered specific SNPs that are useful in detecting metronidazole resistance in *Trichomonas vaginalis*.

BRIEF SUMMARY OF THE INVENTION

The present invention is based on the discovery of particular SNPs in two (2) nitroreductase gene (namely, tvntr4 and tvntr6) in *Trichomonas vaginalis* that represent biomarker candidates for predicting metronidazole resistance in *Trichomonas vaginalis*.

In accordance with the present invention, the presence of at least one of the six (6) SNPs in *Trichomonas vaginalis* (i.e., G76C, C213G and C318A in tvntr4, as well as A238T, G427C, and T476C in tvntr6) represents good markers for the presence of metronidazole resistance. There is disclosed herein methods of detecting these SNPs.

In one aspect, the present invention provides the identification of these novel SNPs to predict the presence of *Trichomonas vaginalis* metronidazole resistance.

In one aspect, the present invention provides a method of detecting metronidazole resistance in *Trichomonas vaginalis* in a human, comprising the steps of: a) obtaining a biological sample from a patient suspected of metronidazole resistance in *Trichomonas vaginalis* infection; b) isolating DNA from said biological sample; and c) detecting the presence of at least one SNP selected from the group consisting of G76C, C213G and C318A in tvntr4 or at least one SNP selected from the group consisting of A238T, G427C, and T476C in tvntr6, wherein the presence of said SNP is indicative of metronidazole resistance in *Trichomonas vaginalis* present in said biological sample.

Preferably, the biological sample is obtained using a cervico-vaginal swab. Preferably, the DNA isolating step is performed using phenol-chloroform. Preferably, the detecting step is performed using a polymerase chain reaction (PCR). Preferably, the detecting step is performed by a real-time PCR followed by sequencing or pyrosequencing. Preferably, the detecting step may be performed by an allele-specific PCR.

In another aspect, the present invention provides a kit for detecting metronidazole resistance in *Trichomonas vaginalis* in a human, comprising: a) a reagent for detecting the presence of a SNP selected from the group consisting of G76C, C213G and C318A in tvntr4, or a SNP selected from the group consisting of A238T, G427C and T476C in tvntr6 in *Trichomonas vaginalis* present in a human; and b) an instruction for use of said reagent in detecting the presence of said SNP, wherein the presence of said SNP is indicative of metronidazole resistance in *Trichomonas vaginalis*.

In one embodiment, the kit contains reagents necessary for the detection of the identified six (6) SNPs. Preferably, the kit contains a forward primer, a reverse primer and a probe that can be used in a real-time PCR. Preferably, the forward primer consists of SEQ ID NO: 5, the reverse primer consists of SEQ ID NO: 6 and the probe consists of SEQ ID NO: 7.

In another embodiment, the kit contains reagents necessary for the detection of the identified six (6) SNPs. Preferably, the kit contains a forward primer, a reverse primer and a probe that can be used in a real-time PCR. Preferably, the forward primer consists of SEQ ID NO: 9, the reverse primer consists of SEQ ID NO: 10 and the probe consists of SEQ ID NO: 11. Preferably, the kit further comprises a reagent for isolating nucleic acid.

BRIEF DESCRIPTION OF THE DRAWINGS

FIG. 1 depicts the nucleic acid alignment of tvntr4 from a metronidazole-susceptible *Trichomonas vaginalis* isolate (G3) and a metronidazole-resistant *Trichomonas vaginalis* isolate (42701). The nucleotide alignment is done using the EBI ClustalW2 Program. Differences in nucleotide sequence from the susceptible *Trichomonas vaginalis* "baseline" are highlighted (in box).

FIG. 2 depicts amino acid alignment of Tvntr4 protein from a metronidazole-susceptible *Trichomonas vaginalis* isolate (G3) and a metronidazole-resistant *Trichomonas vaginalis* isolate (42701). The amino acid alignment is done using the Basic Online Alignment Tool (BLAST). Differences in amino acid sequence from the susceptible *Trichomonas vaginalis* "baseline" are highlighted (in box).

FIG. 3 depicts the nucleotide alignment of primers used for PCR amplification and sequencing of tvntr4.

FIG. 4 depicts the nucleotide alignment of tvntr6 from a metronidazole-susceptible *Trichomonas vaginalis* isolate (G3) and a metronidazole-resistant *Trichomonas vaginalis* isolate (50141). The alignment is done using the EBI ClustalW2 Program. Differences in nucleotide sequence from the susceptible *Trichomonas vaginalis* "baseline" are highlighted (in box).

FIG. 5 depicts amino acid alignment of Tvntr6 protein from a metronidazole-susceptible *Trichomonas vaginalis* isolate (G3) and a metronidazole-resistant *Trichomonas vaginalis* isolate (50141). Differences in sequence from the susceptible *Trichomonas vaginalis* "baseline" are highlighted (in box).

FIG. 6 depicts the nucleotide alignment of primers used for PCR amplification and sequencing of tvntr6 from a metronidazole-resistant *Trichomonas vaginalis* isolate (50141).

FIG. 7 depicts the nucleotide alignment of primers and probes used for real-time PCR detection of the A238T SNP in tvntr6.

FIG. 8 depicts the results of real-time PCR (i.e., amplification plots) for the detection of the A238T SNP in tvntr6.

FIG. 9 depicts the nucleotide alignment of primers used for an alternative method PCR amplification and sequencing of tvntr6 from a metronidazole-resistant *Trichomonas vaginalis* isolate (50141).

DETAILED DESCRIPTION OF THE INVENTION

The present inventors discovered six (6) novel SNP biomarkers useful in predicting the metronidazole resistance in *Trichomonas vaginalis*. To the best of the present inventors' knowledge, there are no reported SNPs shown to be associated with metronidazole resistance in *Trichomonas vaginalis*. These six (6) specific single nucleotide polymorphisms (SNPs) in the tnvtr4 and tvntr6 genes are found to represent good predictors for metronidazole-resistant *Trichomonas vaginalis*.

Definitions:

Various terms used throughout this specification shall have the definitions set forth herein.

The term "*Trichomonas vaginalis*" refers to a haploid protozoan parasite that is a common cause of vaginal infections.

The term "polymorphism" refers to the occurrence of two or more alleles or alternative genomic sequences between or among different genomes.

The term "single nucleotide polymorphism" ("SNP") refers to a site of one nucleotide that varies between alleles.

The term "allele" refers to any of several forms of a gene, usually arising through mutation that is responsible for hereditary variation. An allele is one of a series of different forms of a genetic locus.

The term "oligonucleotide" is used interchangeably with "primer."

The term "primer" refers to an oligonucleotide that acts as a point of initiation of DNA synthesis in a PCR reaction. A primer is usually about 15 to about 35 nucleotides in length and hybridizes to a region complementary to the target sequence.

The term "probe" refers to an oligonucleotide that hybridizes to a target nucleic acid in a PCR reaction. Target sequence refers to a region of nucleic acid that is to be analyzed and comprises the polymorphic site of interest.

The term "genomic material" refers to DNA, RNA or mRNA molecules isolated from a biological sample.

The term "target sequence" refers to a region of nucleic acid that is to be analyzed and comprises the polymorphic site of interest.

The term "biological sample", for purposes of this invention, refers to samples collected from cervico-vaginal or vaginal source. Biological sample often is collected using OneSwab® which is a unique, non-invasive, highly stable specimen collection and transport platform (proprietary to Medical Diagnostic Laboratories, LLC).

The term "allele-specific primer" refers to a DNA primer designed in a way that the 3' base of oligonucleotide matches to only one of the known gene alleles. Allele-specific primers are used for allele-specific amplification and primer extension.

The term "allele-specific PCR" (also known as "allele-specific amplification") refers to a polymerase chain reaction in which at least one of the primers (e.g., allele-specific primer) is chosen from a polymorphic area of gene (e.g., single nucleotide polymorphism), with the polymorphism located at or near the primer's 3'-end. A mismatched primer will not initiate amplification, whereas a matched primer will initiate amplification. The appearance of an amplification product is indicative of the presence of the polymorphism.

The term "real-time PCR" refers to the real-time polymerase chain reaction. Real-time PCR is a method for the detection and quantitation of an amplified PCR product based on a fluorescent reporter dye; the fluorescent signal increases in direct proportion to the amount of PCR product produced and is monitored at each cycle, 'in real time', such that the time point at which the first significant increase in the amount of PCR product correlates with the initial amount of target template.

The term "metronidazole-susceptible" (when used in reference to *Trichomonas vaginalis*) refers to a *Trichomonas vaginalis* isolate that is killed by metronidazole at a concentration less than or equal to 25 micrograms/milliliter (i.e., 25 µg/mL).

The term "metronidazole-resistant" (when used in reference to *Trichomonas vaginalis*) refers to a *Trichomonas vaginalis* isolate that is killed by metronidazole at a concentration greater than or equal to 50 micrograms/milliliter (i.e., 50 µg/mL).

The term "clinical isolate" refers to a cultured *Trichomonas vaginalis* that is isolated from a patient suffering from a *Trichomonas vaginalis* infection.

The term "tvntr3" refers to a gene in the *Trichomonas vaginalis* genome that encodes the *Trichomonas vaginalis* Nitroreductase 3 protein, having the NCBI accession number EAX89567, the disclosure of which is incorporated herein by reference.

The term "tvntr4" refers to a gene in the *Trichomonas vaginalis* genome that encodes the *Trichomonas vaginalis* Nitroreductase 4 protein, having the NCBI accession number EAX94976, the disclosure of which is incorporated herein by reference.

The term "tvntr5" refers to a gene in the *Trichomonas vaginalis* genome that encodes the *Trichomonas vaginalis* Nitroreductase 5 protein, having the NCBI accession number EAX96000, the disclosure of which is incorporated herein by reference.

The term "tvntr6" refers to a gene in the *Trichomonas vaginalis* genome that encodes the *Trichomonas vaginalis* Nitroreductase 6 protein, having NCBI accession number EAX95789, the disclosure of which is incorporated herein by reference.

The term "tvntr9" refers to a gene in the *Trichomonas vaginalis* genome that encodes the *Trichomonas vaginalis* Nitroreductase 9 protein, having NCBI accession number EAY15872, the disclosure of which is incorporated herein by reference.

The term "tvntr10" refers to a gene in the *Trichomonas vaginalis* genome that encodes the *Trichomonas vaginalis* Nitroreductase 10 protein, having NCBI accession number EAY16021, the disclosure of which is incorporated herein by reference.

The term "positive predictive value" refers to the proportion of positive test results that are correct.

The term "positive predictive value" refers to the proportion of negative test results that are correct.

The term "sensitivity" refers to the proportion of positive subjects that are correctly identified.

The term "specificity" refers to the proportion of negative subjects that are correctly identified.

The term "prevalence" refers to proportion of subjects that are positive for a given condition at a given time.

The present invention is directed to the discovery of six (6) novel SNPs present in two (2) nitroreductase genes (i.e., tvntr4 and tvntr6) in *Trichomonas vaginalis*. These SNPs are shown to be associated with the metronidazole resistance in *Trichomonas vaginalis*. The present invention utilizes the application of the correlation of the novel SNPs with metronidazole resistance in *Trichomonas vaginalis*. The present invention provides a method of detecting the presence of the SNPs in a biological sample obtained from a woman suspected of infection of metronidazole resistant *Trichomonas vaginalis*. The presence of the SNPs in the biological sample is indicative of an infection of metronidazole resistant *Trichomonas vaginalis*. Methods of detecting these novel SNPs as well as exemplary primers and probes are also provided herein.

In a first embodiment, the identified SNP is G76C in tvntr4, which causes a corresponding amino acid change of D26H in the Tvntr4 protein.

In a second embodiment, the identified SNP is C213G in tvntr4, which causes a corresponding amino acid change of Y71 STOP in the Tvntr4 protein.

In a third embodiment, the identified SNP is C318A in tvntr4, which causes a corresponding amino acid change of H106Q in the Tvntr4 protein.

In a fourth embodiment, the identified SNP is A238T in tvntr6, which causes a corresponding amino acid change of K80STOP in the Tvntr6 protein.

In a fifth embodiment, the identified SNP is G427C in tvntr6, which causes a corresponding amino acid change of E143Q in the Tvntr6 protein.

In a sixth embodiment, the identified SNP is T476C in tvntr6, which causes a corresponding amino acid change of V159A in the Tvntr6 protein.

Each of these SNP is shown to bear a strong association with metronidzaole resistance in clinical isolates of *Trichomonas vaginalis* and is characterized by having an at least 60% sensitivity or 60% specificity. In accordance with the present invention, identification of the presence of at least one of the six (6) SNPs is indicative of metronidazole resistance in *Trichomonas vaginalis*.

Biological samples of vaginal swab or cervico-vaginal swab in humans are collected by trained medical staffs or physicians under sterile environment. After harvested from patients, biological samples may be immediately frozen (under liquid nitrogen) or put into a storage, or transportation solution to preserve sample integrity. Such solutions are known in the art and commercially available, for example, UTM-RT® transport medium (Copan Diagnostic, Inc, Corona, Calif.), OneSwab® solution, and the like.

Nucleic acids can be conveniently extracted from biological samples obtained from biological tissues or clinical isolates using standard extraction methods that are known in the art. Standard extraction methods include, for example, guanidinium thiocyanate, phenol-chloroform extraction, guanidine-based extraction, and the like. Exemplary nucleic acid purification is provided in Table 1 for illustration purposes only. Commercial nucleic acid extraction kits may also be employed.

Detection of the six (6) identified novel SNPs (e.g., G76C, C213G and C318A in tvntr4 and A238T, G427C and T476C in tvntr6) can be conveniently carried out by a variety of methods known to one skilled in the art. For example, detection of SNP may be performed by a real-time PCR. Preferably, real-time PCR may be performed using exonuclease primers (TaqMan® probes).

One skilled in the art would appreciate many methodologies that can be employed to detect the presence of a SNP present in a particular gene. There are at least two (2) common exemplary methods for detection of products in real-time PCR include: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

PCR amplication (e.g., Real-time PCR or PCR followed by sequencing) can be used to quantify genomic DNA in cells or tissues. Methods suitable for PCR amplification of nucleic acids are known in the art (See, Romero and Rotbart in Diagnostic Molecular Biology Principles and Applications pp. 401-406). PCR reagents and protocols are also available from commercial vendors, such as Roche Molecular Systems. PCR can be performed using an automated process with a PCR machine. One skilled in the art would easily optimize PCR conditions in PCR amplication. Exemplary PCR conditions are provided in Tables 2 and 3 (below). The present invention intends to encompass other PCR amplications that are suitable for the detection of the presence of the identified SNP. The exemplary PCR conditions are therefore not limiting.

Primer sets used in the present PCR reactions for various SNP detection may be prepared or obtained through commercial sources. For purposes of this application, the primer sets used in this invention include primers ordered from Abi (Foster City, Calif.). Preferably, the primers used in the PCR amplification may contain at least 15 nucleotides to 50 nucleotides in length. More preferably, the primers may contain 20 nucleotides to 30 nucleotides in length. One skilled in the art would easily optimize the length of a PCR primer. One skilled in the art would also recognize the optimization of the temperatures of the PCR reaction mixture, number of cycles and number of extensions in the reaction. The amplified product (i.e., amplicons) can be identified by gel electrophoresis. Exemplary PCR primer sets used in various amplication conditions are provided in the Examples of the present application. To this end, primers disclosed in FIGS. 3, 6, 7 and 9 are merely provided for illustration purposes only and therefore are not limiting. It is intended that the application encompass similar primers that can be used and designed by one skilled in the art in their optimization for the detection of the identified novel SNPs.

Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displayed in a graphical format through software developed for real-time analysis.

In addition to the forward primer and reverse primer (conveniently can be obtained via commercial sources), a single-stranded hybridization probe is also used. The hybridization probe may be a short oligonucleotide, usually 20-35 bp in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 bp long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein. Further information on PCR amplification and detection using a Rotor-Gene can conveniently be found on Corbett's website.

The design of primers and probes necessary for performing a PCR in the detection of the identified SNP is readily known by one skilled in the art. The suitable primers utilize the 5' exonuclease activity of thermostable polymerases such as Taq to cleave dual-labeled probes present in the amplification reaction.

The range of the primer concentration can optimally be determined via routine experimentation. The optimization involves performing a dilution series of the primer with a fixed amount of DNA template. The primer concentration may be between about 50 nM to 300 nM. An optimal primer concentration for a given reaction with a DNA template should result in a low Ct-(threshold concentration) value with a high increase in fluorescence (5 to 50 times) while the reaction without DNA template should give a high Ct-value.

The PCR probes used are distinct from the PCR primers. In one embodiment, the PCR probes may be dually-labeled with both a molecule capable of fluorescence and a molecule capable of quenching fluorescence. When the probes are intact, intra-molecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-floruescein moiety and the like. Exemplary quenchers include Black Hole Quencher 1 moiety and the like.

In another embodiment, suitable hybridization probes such as intercalating dye (e.g., Sybr-Green I) or molecular beacon probes can be used. Intercalating dyes can bind to the minor grove of DNA and yield fluorescence upon binding to double-strand DNA. In yet another embodiment, the real-time PCR may include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). The mechanism for molecular beacon probes is based on the proximity of a hairpin structure, a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, Tetrahedron Letts., 22 (20): 1859-1862 using an automated synthesizer, as described in Needham-VanDevanter, D. R., et al. 1984, Nucleic Acids Res., 12: 6159-6168. Purification of oligonucleotides can be performed, e.g., by either native acrylamide gel electrophoresis or by anion-exchange HPLC as described in Pearson, J. D. and Regnier, F. E., 1983, J. Chrom., 255: 137-149.

Other suitable real-time PCR methods include the use of one or more hybridization probes, as determined by those skilled in the art. Exemplary probes such as the HEX channel and/or FAM channel probes, as understood by one skilled in the art.

In yet another embodiment, detection of SNP may be performed using an allele-specific PCR as appreciated by one skilled in the art. Allele-specific PCR method operates on the basis of allele-specific probes. Primers are designed that will anneal to both the mutant (i.e., SNP) and wild-type alleles, and probes are designed that would specifically anneal to either the mutant (i.e., SNP) or the wild-type allele. The probe designed to specifically anneal to the mutant (i.e., SNP) allele is capable of detecting of only metronidazole-resistant *Trichomonas vaginalis* while the probe designed to specifically anneal to the wild-type allele is capable of detecting only metronidazole-sensitive *Trichomonas vaginalis*.

Alternatively, allele-specific PCR method may operate on the basis of the specific amplification of a target allele by the PCR with primers designed such that their 3' ends are placed at the mutation site (i.e., the 3'-most nucleotide of the primer corresponds to the mutated nucleotide in the target/template nucleic acid). When this base is complementary to that of the corresponding nucleotide of the specific allele, the target is amplified; when it is not complementary, PCR will proceed with a significant delay. The longer the delay, the more efficiently the system can discriminate between alleles.

The present invention therefore provides oligonucleotides that are useful for allele-specific PCR. Such oligonucleotides comprise a specificity-enhancing group that improves discrimination between alleles.

The ability to discriminate between alleles by allele-specific PCR may be improved by using DNA polymerases modified to be substantially unable to extend an oligonucleotide when the 3'-most nucleotide of the oligonucleotide is not base paired with the target nucleic acid sequence. The preparation of such modified DNA polymerases is disclosed in WO 99/10366 and WO 98/35060, the contents of which are incorporated herein by reference.

In one embodiment, an allele-specific primer may conveniently be designed based on only one mismatch (based on the polymorphic site) of one of the alleles. The preparation of such allele-specific primers is known in the art and within the capacity of the molecular PCR field.

In another embodiment, an allele-specific primer is designed with a penultimate nucleotide mismatch. Often this second approach may enhance the specificity of the reaction.

In one embodiment, detection of SNP may be performed by sequencing. A variety of automated sequencing procedures (See, e.g., (1995) *Biotechniques* 19:448) may be used. In another embodiment, detection of SNP may be performed by sequencing with the aid of a mass spectrometry (See, e.g., PCT International Publication No. WO94/16101; Cohen et al., *Adv. Chromatogr.* 36:127-162 (1996); and Griffin et al., *Appl. Biochem. Biotechnol.* 38:147-159 (1993)). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

The nucleotide sequence information with respect to the tvntr4 and tvntr6 genes is publically available. One skilled in the art may conveniently design primer sets that would amplify the regions containing the SNPs present on the tvntr4 and tvntr6 genes. A resulting PCR product (i.e., amplicon) of size approximately 300-700 bp is considered to be suitable for sequencing purposes. To perform sequencing, one skilled in the art would employ a sequencing primer in conjunction with a Sequencing Instrument (e.g., ABI 3130 Genetic Analyzer).

In yet another embodiment, detection of SNP may be performed by pyrosequencing. Pyrosequencing comprises a series of steps for the accurate and qualitative analysis of DNA sequences. Pyrosequencing comprises hybridizing a sequencing primer to a single stranded, PCR amplified, DNA template, and incubating the primers and DNA template with the standard PCR enzymes (e.g. DNA polymerase) with ATP sulfurylase, luciferase and apyrase, and the substrates, adenosine 5' phosphosulfate (APS) and luciferin. The first of four (4) deoxyribonucleotide triphosphates (dNTPs) is added to the reaction as a second step. DNA polymerase catalyzes the incorporation of the deoxyribo-nucleotide triphosphate to the complementary base in the target DNA template strand. Each incorporation event is accompanied by release of pyrophosphate (PPi) in a quantity equimolar to the amount of incorporated nucleotide. In the third step, ATP sulfurylase quantitatively converts PPi to ATP in the presence of APS. This ATP drives the luciferase mediated conversion of luciferin to oxyluciferin and generates visible light proportional to the amount of ATP. The light produced in the luciferase-catalyzed reaction is detected by a charge coupled device (CCD) camera and seen as a peak in a Pyrogram™

The height of each peak (light signal) is proportional to the number of nucleotides incorporated. As a fourth step, apyrase, a nucleotide degrading enzyme, continuously degrades ATP and unincorporated dNTPs. This reaction switches off the light and regenerates the reaction solution. The next dNTP is then added one at a time and the process is repeated for each dNTP (i.e. dCTP, dGTP, dTTP) in the fifth step. Deoxyadenosine alfa-thio triphosphate (dATPaS) is used as a substitute for deoxyadenosine triphosphate (dATP) since it is efficiently used y the DNA polymerase, but not recognized by the luciferase. As the process continues, the complementary DNA strand is built up and the nucleotide sequence is determined from the signal peaks in the Pyrogram. Pyrosequencing analytical software assigns both genotype and quantifies the signal strength of each allele. Genotype and signal strength are outputted to standard spreadsheet format. Methods for accomplishing pyrosequencing reactions are well known in the art and are described in, for example, U.S. Pat. Nos. 6,258,568 and 6,258,568.

The present invention provides a method of ascertaining metronidazole resistance om *Trichomonas vaginalis* that is suspected to be present in a biological sample in a human. The biological sample may include for example, cervico-vaginal swab, vaginal swab, and the like. Method of collecting a biological sample is well known. Isolation of DNA from the biological sample is also known. Exemplary DNA isolation includes phenol-chloroform, and the like.

The present inventors have developed a novel molecular method to identify metronidazole-resistant *Trichomonas vaginalis*. The method involves obtaining a small amount of patient samples (e.g., DNA) and utilizing PCR methodology to determine the presence of several SNPs in tvntr4 and tvntr6 genes. The present invention is directed to at least G76C, C213G and C318A in tvntr4 as well as A238T, G427C and T476C in tvntr6.

*Trichomonas vaginalis* infection represents the most common sexually-transmitted disease in the United States (i.e., affecting 3 million women each year). The common use of metronidazole by physicians has increased the metronazole resistant rate (up to 10% of *Trichomonas vaginalis* isolates are resistant to metronidazole). Because *Trichomonas vaginalis* has developed metronidazole resistance, patients infected with these strains are more likely to fail metronidazole treatment. The result of metronidazole resistance leads to more physician visits by the patients, and risk of complications. The standard protocol for assessing metronidazole resistance involves culturing the organisms in a laboratory, where the culture protocol is a highly difficult and can only be performed by a trained technician at the Centers for Disease Control and Prevention. The culture method simply cannot provide metronidazole resistance information in time to guide physicians in their proper patient care. There is an urgent and great need for a molecular assay that can rapidly identify metronidazole resistance in *Trichomonas vaginalis*.

The present assay satisfies the long-felt need in providing physicians with a molecular tool to quickly diagnose whether the patient is infected with metronizale-resistant *Trichomonas vaginalis*. The present invention offers clinicians with various treatment options for the patients. For example, if a woman is determined to have infected with metronizale-resistant *Trichomonas vaginalis*, a higher-dose of metronidazole, a longer treatment duration of metronidazole or use of an alternate drug (e.g., timidazole) may represent alternative treatment options.

Another advantage of the present invention is a more effective patient treatment, and a reduction in repeated physician visits; thereby reduces healthcare costs.

Kits

The present invention also provides a kit of manufacture, which may be used to perform detecting the presence of a SNP of G76C, C213G or C318A in tvntr4, or a SNP of A238T, G427C or T476C in tvntr6. The presence of these SNP is shown to associate with (i.e., indicative of) of metronidazole resistance in *Trichomonas vaginalis* present in said biological sample. In one embodiment, an article of manufacture (i.e., kit) according to the present invention includes a set of primers (i.e., a forward primer and a reverse primer) directed to a specific region of the tvntr4 and tvntr6 gene for its detection of the particular SNP. Optionally, a hybridization probe is included in the kit for detection of PCR product.

The present invention provides the identified six (6) novel SNPs. Detection of these SNP can be performed using a commercial kit that contains necessary reagents. One skilled in the art would conveniently design the primer sets necessary for detecting the presence of a SNP. These SNPs include G76C, C213G and C318A in tvntr4, or A238T, G427C and T476C in tvntr6 in *Trichomonas vaginalis*.

In one embodiment, the kit contains reagents necessary for the detection of the identified six (6) SNPs using a real-time PCR. Preferably, the kit contains a forward primer, a reverse primer and a probe that can be used in a real-time PCR. Preferably, the forward primer consists of SEQ ID NO: 5, the reverse primer consists of SEQ ID NO: 6 and the probe consists of SEQ ID NO: 7.

In another embodiment, the kit contains reagents necessary for the detection of the identified six (6) SNPs. Preferably, the kit contains a forward primer, a reverse primer and a probe that can be used in a real-time PCR. Preferably, the forward primer consists of SEQ ID NO: 9, the reverse primer consists of SEQ ID NO: 10 and the probe consists of SEQ ID NO: 11. Preferably, the kit further comprises a reagent for isolating nucleic acid.

In yet another embodiment, the present invention intends to encompass a kit containing reagents necessary for the detection of the identified six (6) SNPs using other methodologies such as allele-specific PCR, PCR followed by sequencing or PCR followed by pyrosequencing.

Kits provided herein may also include instructions, such as a package insert having instructions thereon, for using the reagents (e.g., primers) to quantify the presence of a particular SNP in tvntr4 and tvntr6 in a biological sample. Such instructions may be for using the primer pairs and/or the hybridization probes to specifically detect the presence of a specific SNP (i.e., G76C, C213G or C318A in tvntr4, or a SNP of A238T, G427C or T476C in tvntr6).

In one embodiment, the kit further comprises reagents used in the preparation of the biological sample to be tested for presence of SNP in tvntr4 and tvntr6 (e.g. lysis buffer).

In another embodiment, the kit comprises reagents used in the preparation of the sample to be tested for genomic DNA (e.g., guanidinium thiocyanate or phenol-chloroform extraction).

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

EXPERIMENTAL STUDIES

Example 1

Sequencing of tvntr Genes Encoding *Trichomonas vaginalis* Nitroreductase (Tvntr) Proteins a) tvntr1-12 genes in *Trichomonas vaginalis*

Pal et al. in 2009 described that the Tvntr8 protein reduces and thus activates metronidazole in vitro. Tvntr8 protein is encoded by the tvntr8 gene, which represents one (1) of the 12 *Trichomonas vaginalis* nitroreductase genes.

In this study, we sought to sequence all 12 tvntr genes in *Trichomonas vaginalis*. We selected a total of 100 clinical isolates of *Trichomonas vaginalis*; namely, 50 metronidazole-susceptible clinical isolates and 50 metronidazole-resistant clinical isolates. These clinical isolates were used to amplify DNA for sequencing. To do so, we extracted the genomic DNA from these clinical isolates by lysis with an anionic detergent (1% SDS and 2% Triton-X 100) followed by extraction with phenol-chloroform and precipitation with ethanol (See, Table 1 in the "Experimental Methods and Protocols" section). Primers (and their nucleotide sequences) used for amplifying the extracted genomic DNA are shown in Table 9. PCR conditions for amplifying the extracted genomic DNA are shown in Table 2.

The resulting PCR products were subject to sequence analysis using the ABI3130 Genetic Analyzer with the sequencing protocol as detailed in Table 3. We used the Megalign program from Lasergene to align the sequences of the metronidazole-susceptible and metronidazole-resistant clinical isolates for the respective tvntr genes.

b) Sequence Alignment and SNP Analysis

FIG. 1 shows the nucleotide sequence alignment for tvntr4 between metronidazole-susceptible and metronidazole-resistant clinical *Trichomonas vaginalis* isolates.

FIG. 4 shows the nucleotide sequence alignment for tvntr6 between metronidazole-susceptible and metronidazole-resistant clinical *Trichomonas vaginalis* isolates. Single nucleotide polymorphisms between metronidazole-susceptible and metronidazole-resistant isolates are boxed in black. (See, FIGS. 1 and 7 for tvntr4 and tvntr6, respectively).

The resulting single nucleotide polymorphisms (SNPs) are summarized in Table 4. Our discovery of several SNPs within the tvntr3, tvntr4, tvntr6, tvntr9 and tvntr10 genes of metronidazole-resistant *Trichomonas vaginalis* presents an opportunity to evaluate these SNPs as potential molecular biomarkers for diagnosis of metronidazole-resistant *Trichomonas vaginalis*.

Example 2

Single Nucleotide Polymorphisms (SNPs) in *Trichomonas vaginalis* Tvntr3, Tvntr9 and Tvntr10 Genes and their Association with Metronidazole-Resistance We examined the validity of the following SNPs as biomarkers for detecting metronidazole-resistant *Trichomonas vaginalis*. In this study, using the 100 clinical isolates of *Trichomonas vaginalis* (i.e., fifty (50) metronidazole-resistant isolates and fifty (50) metronidazole-susceptible isolates), we specifically examined the presence of A176T, G199A, G214A, G274A, A385G, T506C and A515C in tvntr3; C288I and T350C in tvntr9; and T395C in tvntr10 in the clinical isolates. None of these SNPs demonstrated any significant associations with metronidazole resistant *Trichomonas vaginalis* (See, Table 4). We concluded, based on the selected SNPs in tvntr3, tvntr9, and tvntr10 genes, that these genes do not have an association with metronidazole resistance in *Trichomonas vaginalis*.

Example 3

Single Nucleotide Polymorphisms (SNPs) in *Trichomonas vaginalis* Tvntr4 and Tvntr6 Genes and their Association with Metronidazole-Resistance We continued to examine the validity of the following SNPs as biomarkers for detecting metronidazole-resistant *Trichomonas vaginalis*; namely, G76C, C213G and C318A in tvntr4 or A238T, G427C and T476C in tvntr6.

In this study (as described in Example 2), we used the one-hundred (100) clinical *Trichomonas vaginalis* isolates (i.e., fifty (50) metronidazole-resistant isolates and fifty (50) metronidazole-susceptible isolates). Resistance or susceptibility of the clinical isolates to metronidazole was determined by broth dilution assay. Isolates with minimum lethal concentration (MLC) values of ≥50 micrograms/milliliter (μg/ml) of metronidazole were considered resistant, whereas isolates with MLC values of ≤25 μg/ml of metronidazole were considered susceptible.

Cultures were grown and DNA was extracted, as described in Table 1. Table 1 provides the protocol used for growing *Trichomonas vaginalis* and extracting DNA. Extracted DNA was used for PCR reactions described within this patent. Purity of the genomic DNA was confirmed by spectrophotometry ($A_{260}/A_{280}$).

PCR amplification of tvntr4 and tvntr6 from clinical *Trichomonas vaginalis* isolates was carried out using primer sets from Table 9 and methods described in Table 2. Table 2 provides a protocol for the PCR amplification of a part of the tvntr4 or tvntr6 gene of *Trichomonas vaginalis* from genomic DNA. High fidelity Taq Polymerase was used to ensure that any polymorphisms observed were true to the organism and not attributable to a low fidelity polymerase.

Resulting amplicons were purified using the Stratagene PCR Purification Kit as described by the manufacturer in order to have the purest DNA to sequence. DNA sequencing was performed using the ABI 3130 Genetic Analyzer as described by the manufacturer using the methods described in Table 3. Nucleotide sequences obtained were entered into the NCBI BLAST program described previously and aligned to the available reference sequences to ensure that the sequencing was successful. If the sequencing was successful, the nucleotides at position 76, 123 and 318 in tvntr4, and 238, 427 and 476 in tvntr6 were examined for the presence of changes indicative of metronidazole resistance.

The results are summarized in Table 4 as follows: tvntr4 G76C was present in 30 out of 50 resistant isolates and in 16 out of 50 susceptible isolates, tvntr4 C213G was present in 33 out of 50 resistant isolates and in 17 out of 50 susceptible isolates, tvntr4 C318A was present in 24 out of 50 resistant isolates and in 12 out of 50 susceptible isolates. tvntr6 A238T was present in 20 out of 50 resistant isolates and 2 out of 50 susceptible isolates, tvntr6 G427C was present in 38 out of 50 resistant isolates and in 17 out of 50 sensitive isolates, and tvntr6 T476C was present in 20 out of 50 resistant isolates and in 2 out of 50 sensitive isolates. From these studies, we concluded that these six (6) SNPs in tvntr4 and tvntr6, unlike those in tvntr3, tvntr9 and tvntr10, can serve as good biomarkers as indicative of metronidazole resistance in *Trichomonas vaginalis*.

Example 4

Statistical Analyses

We performed statistical analyses on the sequence data obtained for tvntr4 and tvntr6 from clinical *Trichomonas vaginalis* isolates. The methods used to derive these statistics are described in Table 5. Sensitivity and specificity for detection of *Trichomonas vaginalis* metronidazole resistance was determined for each individual SNP (Table 6).

The presence of tvntr4 C213G detects metronidazole resistance with 66% sensitivity and 66% specificity, the presence of tvntr4 G76C detects metronidazole resistance with 60% sensitivity and 68% specificity, the presence of tvntr4 C318A detects metronidazole resistance with 48% sensitivity and 76% specificity.

The presence of tvntr6 A238T detects metronidazole resistance with 40% sensitivity and 96% specificity, and the presence of tvntr6 G427C detects metronidazole resistance with 76% sensitivity and 66% specificity, the presence of tvntr6 T476C detects metronidazole resistance with 40% sensitivity and 96% specificity.

The positive predictive value (PPV), or proportion of subjects with positive test results that are correctly identified, and the negative predictive value (NPV), or proportion of subjects with negative test results that are correctly identified, were also determined (Table 7).

For the detection of metronidazole resistance, the presence of tvntr4 C213G has a PPV of 65% and an NPV of 63%, the presence of tvntr4 G76C has a PPV of 66% and an NPV of 66%, the presence of tvntr4 C318A has a PPV of 67% and an NPV of 59%, the presence of tvntr6 A238T has a PPV of 91% and an NPV of 62%, the presence of tvntr6 G427C has a PPV of 69% and an NPV of 73%, and the presence of tvntr6 T476C has a PPV of 91% and an NPV of 62%.

The statistical significance of the association between individual SNPs was determined by the two-tailed Fisher's exact test comparing the prevalence of the SNP in metronidazole-resistant and metronidazole-susceptible isolates, and values <0.05 are considered significant (Table 8). The P value was 0.0088 for tvntr4 C213G, 0.0025 for of tvntr4 G76C, 0.021 for tvntr4 C318A, 0.000017 for tvntr6 A238T, 0.000046 for tvntr6 G427C and 0.000017 for tvntr6 T476C.

The results are summarized as follows. Detection of tvntr4 G76C and tvntr6 G427C resulted in 66% sensitivity, 74% specificity, 72% PPV and 69% NPV. Detection of tvntr4 C213G, tvntr4 G76C or tvntr6 G427C resulted in 60% sensitivity, 76% specificity, 71% PPV and 66% NPV.

Example 5

Use of Real-Time PCR for the Detection of A238T SNP in *Trichomonas vaginalis* Tvntr6

In this study, we have developed a real-time PCR assay to detect A238T SNP in tvntr6 of *Trichomonas vaginalis*. Here, we used a real-time PCR for the detection of SNPs. We designed primers that annealed to both the A238 and T238 tvntr6 alleles, and probes that would anneal to either the A238 or the T238 tvntr6 alleles. Table 9 summarizes the primers and probes. The real-time PCR reaction is described in Table 10.

The real-time PCR was found to be sensitive in detecting the presence of A238T SNP. FIG. 4 shows the detection of only the metronidazole-sensitive *Trichomonas vaginalis* isolate with the A238 probe and detection of only the metronidazole-resistant *Trichomonas vaginalis* isolate with the T238 probe.

Example 6

Use of PCR Amplification and Sequencing as a Method to Detect the Tvntr4 G76C, C213G and C318A SNPs, and the Tvntr6 A238T, G427C and T476C SNPs In this study, we developed a PCR amplification and sequencing as a method for the detection of the identified novel SNPs in *Trichomonas vaginalis*. As described in Example 1, we used this alternative assay to detect the tvntr4 G76C, C213G and C318A SNPs or the tvntr6 A238T, G427C and T476C SNPS from a sample is to amplify a segment or the entire gene via polymerase chain reaction (PCR) using a high fidelity DNA Polymerase (Tables 1 and 2). The resulting PCR product can be run in a cycle sequencing reaction (Table 3) and the sequence can be read using specialized equipment, such as the ABI 3130 Genetic Analyzer. PCR amplification and sequencing allow the direct visualization of the nucleotide present at each position within the gene amplified.

Example 7

Detection of Tvntr6 A238T SNP Using an Alternate Qualitative Real-Time PCR Method In this study, we developed an improved qualitative real-time PCR method to detect the tvntr6 A238T SNP. We used this improved method in a blind challenge study to further evaluate the presence of tvntr6 in clinical isolates. To that end, we obtained 100 new clinical isolates (separated from those described in the above Examples), provided by the Centers for Disease Control and Prevention. The clinical isolates used in the present blind challenge experiment are summarized in Table 11. Note that these clinical isolates were provided without confidential clinical information relating to their metronidazole resistance.

The detailed reaction condition for the real-time PCR is provided in Table 12. In this improved real-time PCR, we used a specific primer pair and probe, the nucleotide sequences of which are listed in Table 9. The alignment of these oligonucleotides with the tvntr6 sequence is depicted in FIG. 9.

The results of the blind challenge study are summarized in Table 13. In this study, we were able to detect the tvntr6 A238T SNP in 15/49 metronidazole-resistant isolates and 2/51 metronidazole-susceptible isolates. The assay provided a sensitivity of 31% and a specificity of 96%.

EXPERIMENTAL METHODS AND PROCEDURES a) Clinical Isolates of *Trichomonas vaginalis*

*Trichomonas vaginalis* isolates were obtained from the American Type Culture Collection (ATCC) or the Centers for Disease Control and Prevention (CDC). Cervico-vaginal swabs were obtained from discarded human samples used for molecular testing at Medical Diagnostic Laboratories. *Trichomonas vaginalis* cultures were grown in TYM media (per 900 ml: 20 grams peptone from casein, 10 grams yeast extract, 5 grams maltose, 1 gram L-cysteine, 0.2 gram L-ascorbic acid, 0.8 gram $K_2HPO_4$, 0.8 gram $KH_2PO_4$, 0.5 gram Agar; adjusted to pH 6.0 and autoclaved) with 5% heat-inactivated horse serum, 100 U/ml penicillin and 100 µg/ml streptomycin. Cultures of *Trichomonas vaginalis* were incubated at 37° C. under anaerobic conditions.

b) DNA Extraction

For DNA isolation, cells were pelleted, washed with PBS, and re-suspended in breaking buffer (2% Triton X-100, 1% SDS, 100 mM NaCl, 10 mM Tris pH 8, 1 mM EDTA) to which acid-washed glass beads were added. Three phenol-chloroform extractions were performed, and the aqueous layers were removed and DNA precipitated with ethanol and sodium acetate. The pellet was washed with cold ethanol, dissolved in nuclease-free water and stored at −20° C. DNA extracted from OneSwab® transport medium by either the X-tractor Gene automated nucleic acid extraction system (Corbett Robotics) according to the manufacturer's instructions.

c) Detection of tvntr SNPs by PCR Amplification and Sequencing

The tvtnr4 and tvntr6 genes were amplified with USB Taq polymerase with 500 µM dNTP's, 625 nM each oligonucleotide and 2.5 mM $MgCl_2$ added to the reactions. In our PCR assay for tvntr4 and tvntr6, we employed a pair of primer set (i.e., SEQ ID NO 1 and SEQ ID NO 2) to amplify tvntr4, and another pair of primer set (i.e., SEQ ID NO 3 and SEQ ID NO 4) to amplify tvntr6. The PCR reaction conditions were as follows: 95° C. for 5 minutes; 35 cycles of 95° C. for 1 minute, 50° C. for 1 minute and 68° C. for 2 minutes; 68° C. for 5 minutes. The PCR products were analyzed by acrylamide gel electrophoresis and purified using the Wizard® SV Gel and PCR Clean-Up System (Promega) according to the manufacturer's instructions.

Sequences of PCR products were determined using the ABI3130 genetic analyzer (Applied Biosystems) as per the manufacturer's instructions. Sequence information was analyzed by BLAST to detect SNPs.

d) Detection of Tvntr6 A238T SNP by Real-Time PCR

PCR Reactions were prepared using 1 µl of template DNA mixed with 20 nM of SEQ ID. NO: 5, 20 nM of SEQ. ID. NO: 6, 0.8 nM SEQ. ID. NO: 7 and 0.8 nM SEQ ID NO 8 in Quanta Perfecta SuperMix for iQ (Bio-Rad). Reactions conditions were 95° C. for 2 minutes and then 35 cycles of 95° C. for 15 seconds and 63° C. for 30 seconds. Reactions were performed in a Stratagene Mx3000p QPCR System (Agilent), capturing JOE and FAM fluorescence.

e) Detection of Tvntr6 A238T SNP by an Alternate Real-Time PCR Method

PCR Reactions were prepared using 1 μl of template DNA mixed with 500 nM of SEQ. ID. NO: 9, 500 nM of SEQ. ID. NO: 10 and 333 nM of SEQ. ID. NO: 11 in Quanta Perfecta AccuQuant Custom Supermix (Quanta). Reaction conditions were 95° C. for 2 minutes and then 35 cycles of 95° C. for 15 seconds and 63° C. for 45 seconds. Reactions were performed in a Rotor Gene RG-3000 (Corbett Robotics), reading fluorescence on FAM.

f) Statistical Methods

The following equations were used to determine the sensitivity, specificity, positive predictive value, and negative predictive value for the ability of tvntr SNPs predict *Trichomonas vaginalis* metronidazole resistance. Statistical methods used are from Altman D G, Bland J M (1994). "Diagnostic tests. 1: Sensitivity and specificity" *BMJ* 308 (6943): 1552.

$$a) \text{ Sensitivity } \% = \frac{No. \text{ of True Positives}}{No. \text{ True Positives} + \# \text{ False Negatives}} * 100$$

$$b) \text{ Specificity } \% = \frac{No. \text{ of True Negatives}}{No. \text{ True Negatives} + No. \text{ False Positives}} * 100$$

$$c) \text{ Positive Predictive Value } \% = \frac{No. \text{ of True Positives}}{No. \text{ True Positives} + No. \text{ False Positives}} * 100$$

$$d) \text{ Negative Predictive Value } \% = \frac{No. \text{ of True Negatives}}{No. \text{ True Negatives} + No. \text{ False Negatives}} * 100$$

$$e) \text{ Two-tailed Fisher's Exact Test} = p = \frac{\binom{a+b}{a}\binom{c+d}{c}}{\binom{n}{a+c}}$$

where a, b, c, and d are the values contained within a 2×2 contingency table.

TABLE 1

Genomic DNA purification Protocol
DNA Extraction Protocol

1. Cultures were grown in TYM media (Per 900 ml: 20 g peptone from casein, 10 g yeast extract, 5 g maltose, 1 g L-cysteine, 0.2 g L-ascorbic acid, 0.8 g $K_2HPO_4$, 0.8 g $KH_2PO_4$, 0.5 g Agar; adjust to pH 6.0 and autoclave to sterilize). Glass culture tubes containing 9 ml TYM medium, 500 ul heat-inactivated horse serum, 100 U/ml penicillin and 100 μg/ml streptomycin were pre-reduced in an anaerobic chamber for 24 hours prior to inoculating cultures. One milliliter of a frozen stock ($10^6$ cells in TYM media with 5% DMSO) from ATCC or CDC was added to a culture tube of media and incubated at 37° C. in an anaerobic chamber.
2. Motile cells were counted on hemocytometer to obtain $1 \times 10^6$ cells. Culture was added to 1.5 ml centrifuge tubes and centrifuged at 14,000x g for 2 minutes.
3. Supernatant was removed and washed with PBS. Centrifugation was repeated.
4. Pellet was re-suspended in 200 ul of breaking buffer (2% TritonX-100, 1% SDS, 100 mM NaCl, 10 mM Tris pH 8, 1 mM EDTA), then 200 ul of acid-washed glass beads was added.
5. 200 ul of Phenol-Chloroform-Isoamyl Alcohol (25:24:1) was added to the tube and vortexed for 2 minutes.
6. 200 ul of TE buffer was added to the tube which was inverted to mix.
7. The tube was centrifuged at 14,000x g for 10 minutes.
8. The aqueous layer was transferred to a new centrifuge tube, avoiding the interface.
9. The Phenol-Chloroform extraction step was repeated two more times.
10. 1 ml cold 95% ethanol and 75 ul 3M Na-Acetate was added to the tube containing the aqueous layer. The tube was inverted to mix and stored at −20° C. for 1 hour.
11. After 1 hour, the tube was centrifuged for 10 minutes at room temperature, then the supernatant was poured off.
12. The pellet was washed with 1 ml of cold 70% ethanol (without re-suspending the pellet) by centrifuging at 14,000x g for 5 minutes at room temperature, then the supernatant was poured off.
13. The pellet was dried for 30 minutes to evaporate remaining ethanol.
14. The pellet was re-suspended in nuclease free water, tapping tube to dissolve.
15. The DNA was stored at −20° C.

TABLE 2

PCR Amplification of tvntr4 and tvntr6

| Master Mix | |
|---|---|
| USB 10x PCR Buffer (+2.5 mM MgCl) | 4 ul |
| dNTPs (10 mM) | 0.8 ul |
| F Primer (50 uM) | 0.5 ul |
| R Primer (50 uM) | 0.5 ul |
| USB Fidelitaq | 0.5 ul |
| Nuclease-free water | 31.7 ul |
| Extracted DNA | 2 ul |
| | 40 ul |

| Thermal Profile | | |
|---|---|---|
| Step | Temp (° C.) | Time |
| 1 | 95 | 5 min |
| 2 | 95 | 1 min |
| 3 | 50 | 1 min |
| 4 | 68 | 2 min |
| 5 | 68 | 5 min |
| 6 | 4 | hold |

*Repeat steps 2-4 for 35 cycles 20 ul of the PCR product was run on a 1.5% agarose gel to verify the size of the amplicon. The remaining 20 ul was purified for sequencing using the Promega Wizard SV Gel and PCR Clean-Up System.

TABLE 3 tvntr4 and tvntr6 Sequencing PCR
Sequences of PCR products were analyzed using ABI3130
genetic analyzer (Applied Biosystems, Foster City, CA)

| Master Mix | |
|---|---|
| Terminator Ready Reaction Mix v1.1 | 8 ul |
| Primer (50 uM) | 0.6 ul |
| Nuclease-free water | 4.9 ul |
| Purified PCR product | 6.5 ul |
| | 20 ul |

| Thermal Profile | | |
|---|---|---|
| Step | Temp (° C.) | Time |
| 1 | 96 | 1 Min |
| 2 | 96 | 10 sec |
| 3 | 50 | 5 sec |
| 4 | 60 | 4 Min |
| 5 | 4 | hold |

* Repeat steps 2-4 for 25 cycles

TABLE 4

Summary of *Trichomonas vaginalis* Nitroreductase (tvntr) Gene SNPs

| Gene | SNP | Amino Acid Change | Resistant Isolates Positive | Resistant Isolates Negative | Sensitive Isolates Positive | Sensitive Isolates Negative |
|---|---|---|---|---|---|---|
| tvntr3 | A176T | Q59L | 1 | 31 | 0 | 33 |
| | G199A | G67R | 21 | 11 | 22 | 10 |
| | G214A | G72R | 0 | 32 | 2 | 31 |
| | G274A | D92N | 9 | 23 | 4 | 30 |
| | A385G | S129G | 31 | 1 | 33 | 1 |
| | T506C | L169P | 0 | 32 | 2 | 32 |
| | A515C | E171A | 0 | 32 | 1 | 33 |
| tvntr4 | T152A | V51D | 3 | 47 | 5 | 45 |
| | G208C | E70Q | 3 | 47 | 5 | 45 |
| | G76C | D26H | 30 | 20 | 16 | 34 |
| | C213G | Y71STOP | 33 | 17 | 17 | 33 |
| | C318A | H106Q | 24 | 26 | 12 | 38 |
| tvntr6 | G259A | E87K | 6 | 44 | 1 | 49 |
| | T458C | V153A | 1 | 49 | 1 | 49 |
| | A238T | K80STOP | 20 | 30 | 2 | 48 |
| | G427C | E143Q | 38 | 12 | 18 | 32 |
| | T476C | V159A | 20 | 30 | 2 | 48 |
| tvntr9 | C288A | F96L | 1 | 26 | 0 | 28 |
| | T350C | V117A | 4 | 23 | 0 | 27 |
| tvntr10 | T395C | V132A | 0 | 17 | 1 | 6 |

TABLE 5

Derivation of Statistics
Showing the statistical derivation of sensitivity, specificity, positive predictive value, and negative predictive value for the ability of tvntr SNPs predict *Trichomonas vaginalis* metronidazole resistance. Statistical methods used are from Altman D. G., Bland J. M. (1994). "Diagnostic tests. 1: Sensitivity and specificity" *BMJ* 308 (6943): 1552.

a) $\text{Sensitivity \%} = \dfrac{\text{\# of True Positives}}{\text{\# True Positives} + \text{\# False Negatives}} * 100$ b) $\text{Specificity \%} = \dfrac{\text{\# of True Negatives}}{\text{\# True Negatives} + \text{\# False Positives}} * 100$ c) $\text{Positive Predictive Value \%} = \dfrac{\text{\# of True Positives}}{\text{\# True Positives} + \text{\# False Positives}} * 100$ d) $\text{Negative Predictive Value \%} = \dfrac{\text{\# of True Negatives}}{\text{\# True Negatives} + \text{\# False Negatives}} * 100$ e) Two-tailed Fisher's Exact Test =

$$p = \dfrac{\binom{a+b}{a}\binom{c+d}{c}}{\binom{n}{a+c}}$$

where a, b, c, and d are the values contained within a 2×2 contingency table.

TABLE 6

Sensitivity and Specificity of tvntr SNPs

| Gene | SNP | Sensitivity | Specificity |
|---|---|---|---|
| tvntr4 | G76C | 60 | 68 |
| | C213G | 66 | 66 |
| | C318A | 48 | 76 |
| tvntr6 | A238T | 40 | 96 |
| | G427C | 76 | 66 |
| | T476C | 40 | 96 |

TABLE 7

Positive Predictive Value (PPV) and Negative Predictive Value (NPV) for tvntr SNPs

| Gene | SNP | Positive Predictive Value (PPV) | Negative Predictive Value (NPV) |
|---|---|---|---|
| tvntr4 | G76C | 65 | 63 |
| | C213G | 66 | 66 |
| | C318A | 67 | 59 |
| tvntr6 | A238T | 91 | 62 |
| | G427C | 69 | 73 |
| | T476C | 91 | 62 |

TABLE 8

Significant Associations of tvntr SNPs

| Gene | SNP | P value |
|---|---|---|
| tvntr4 | G76C | 0.0088 |
| | C213G | 0.0025 |
| | C318A | 0.021 |
| tvntr6 | A238T | 0.000017 |
| | G427C | 0.000046 |
| | T476C | 0.000017 |

TABLE 9

Primers and Probes for Detection of tvntr6 A238T

| Oligonucleotide | Description | Sequence |
|---|---|---|
| SEQ ID NO 1 | tvntr4 Forward Primer | ATGAGTGTCCTTAAGTGCATCCAA |
| SEQ ID NO 2 | tvntr4 Reverse Primer | TTAGTCGGCATAAACTACCTTAGA |
| SEQ ID NO 3 | tvntr6 Forward Primer | CATTGAATTTATTCGTTCAAAATT |
| SEQ ID NO 4 | tvntr6 Reverse Primer | TTATTCAATGTATGTAACCTTTCT |
| SEQ ID NO 5 | tvntr6 Real-Time Forward Primer | CTCCATCAGCTATGAATGTTCAGG |
| SEQ ID NO 6 | tvntr6 Real-Time Reverse Primer | GGAATCAAGTTGTTGAATGGCTGG |
| SEQ ID NO 7 | tvntr6 A238 Probe | /56-JOEN/TGGAATGCAAAAGCAGACACATGT/3BHQ2/ |
| SEQ ID NO 8 | tvntr6 T238 Probe | /56-FAM/TGGAATGCAATAGCAGACACATGT/3BHQ2/ |
| SEQ ID NO 9 | Tvntr6 Alternate Method Real-Time Forward Primer | CGTTGTTACAAACAAGGAAAAACTCC |
| SEQ ID NO 10 | Tvntr6 Alternate Method Real-Time Reverse Primer | GGATGCACGCTCATTCTTGA |
| SEQ ID NO 11 | Tvntr6 Alternate Method Real-Time T238 Probe | /56-FAM/TGGAATGCAATAGCAGACACATGT/BHQ2/ |

TABLE 10

Real-time PCR to detect the tvntr6 A238T SNP

Master Mix

| | |
|---|---|
| Quanta Perfecta SuperMix for iQ | 10 µl |
| ddH$_2$O | 8.04 µl |
| SEQ ID 7 (1 µM) | 0.4 µl |
| SEQ ID 8 (1 µM) | 0.4 µl |
| SEQ ID 9 (200 nM) | 0.08 µl |
| SEQ ID 10 (200 nM) | 0.08 µl |
| DNA | 1.0 µl |
| Total | 20 µl |

Thermal Profile

| Step | Temp | Time |
|---|---|---|
| 1 | 95° C. | 2 min |
| 2 | 95° C. | 15 sec |
| 3 | 63° C. | 30 sec |

*repeat steps 2-3 for 35 cycles

Read using Stratagene Mx3000p, reading fluorescence on FAM and JOE channels

Amplification as shown by JOE fluorescence indicates the A238 allele. Amplification as shown by FAM fluorescence indicates the T238 allele.

TABLE 11

Trichomonas vaginalis Isolates

I. ATCC Isolates: *Trichomonas vaginalis* isolates PRA-98 and 30001 (metronidazole susceptible) and 50141, 50142, and 50143 (metronidazole resistant) were obtained from the American Type Culture Collection (ATCC).

II. CDC Isolates: *Trichomonas vaginalis* isolates were obtained from the Trichomoniasis Lab at the Centers for Disease Control and Prevention (CDC). Aerobic MLC data was provided by the CDC and strains were classified as metronidazole susceptible (≤25 ug/ml) or resistant (≥100 ug/ml). Lines 1-50: Isolates used for SNP discovery. Lines 51-101: Isolates used for blind challenge.

| Line | ID #s Resistant | Upper Value Metronidazole (µg/ml) | ID #s Susceptible | Upper Value Metronidazole (µg/ml) |
|---|---|---|---|---|
| 1 | 50141 * | 200 | PRA-98 * | 1 |
| 2 | 50142 * | 125 | 30001 * | 8 |
| 3 | 50143 * | 150 | WA07130902 | 1.6 |
| 4 | 1178 | 200 | WA06150905 | 3.1 |
| 5 | 1179 | 200 | WA07130906 | 0.8 |
| 6 | 1181 | 100 | WA06020908 | 1.6 |
| 7 | 1184 | 100-200 | WA06020910 | 1.6 |
| 8 | 1185 | 400 | WA05110911 | 0.8 |
| 9 | 1188 | >400 | WA05110913 | 6.3 |
| 10 | 1189 | 400 | WA05110918 | 1.6 |
| 11 | 1190 | >400 | SF-09042701 | 6.3 |
| 12 | 1191 | 400 | SF-09042801 | 1.6 |
| 13 | 1192 | >400 | SF-09050402 | 1.6 |
| 14 | 1200 | 400 | SF-09051101 | 1.6 |
| 15 | 1201 | >400 | SF-09060101 | 12.5 |
| 16 | 1202 | 400 | SF-09060901 | 6.3 |
| 17 | 1203 | >400 | SF-09061501 | 6.3 |

TABLE 11-continued

*Trichomonas vaginalis* Isolates
I. ATCC Isolates: *Trichomonas vaginalis* isolates PRA-98 and 30001 (metronidazole susceptible) and 50141, 50142, and 50143 (metronidazole resistant) were obtained from the American Type Culture Collection (ATCC).
II. CDC Isolates: *Trichomonas vaginalis* isolates were obtained from the Trichomoniasis Lab at the Centers for Disease Control and Prevention (CDC). Aerobic MLC data was provided by the CDC and strains were classified as metronidazole susceptible (≤25 ug/ml) or resistant (≥100 ug/ml). Lines 1-50: Isolates used for SNP discovery. Lines 51-101: Isolates used for blind challenge.

| Line | ID #s Resistant | Upper Value Metronidazole (µg/ml) | ID #s Susceptible | Upper Value Metronidazole (µg/ml) |
|---|---|---|---|---|
| 18 | 1205 | 200-400 | SF-09061601 | 12.5 |
| 19 | 1208 | 200 | SF-09062401 | 3.1 |
| 20 | 1209 | 400 | SF-09063001 | 3.1 |
| 21 | 1210 | 400 | SF-09070801 | 3.1 |
| 22 | 1212 | 400 | SF-09073001 | 12.5 |
| 23 | 1213 | 400 | SF-09080302 | 1.6 |
| 24 | 1214 | 400 | SF-09081001 | 25 |
| 25 | 1215 | 400 | SF-09081002 | 1.6 |
| 26 | 1216 | 200 | SF-09081003 | 12.5 |
| 27 | 1217 | 400 | SF-09081101 | 0.8 |
| 28 | 1219 | 100 | SF-09081102 | 3.1 |
| 29 | 1220 | 400 | SF-09081103 | 1.6 |
| 30 | 1222 | 200-400 | CO-113208 | 25 |
| 31 | 1224 | 100 | CO-113124 | 12.5 |
| 32 | 1225 | >400 | CO-113632 | 3.1 |
| 33 | 1107 | >400 | CO-113328 | 6.3 |
| 34 | 1109 | >400 | CO-113353 | 1.6 |
| 35 | 1110 | 200 | CO-113289 | 12.5 |
| 36 | 1112 | 400 | CO-112435 | 1.6 |
| 37 | 1113 | 100 | CO-113031 | 1.6 |
| 38 | 1115 | 200 | CO-112673 | 1.6 |
| 39 | 1116 | 200 | CO-112062 | 12.5 |
| 40 | 1117 | 200 | CO-112362 | 1.6 |
| 41 | 1118 | 200 | CO-112068 | 1.6 |
| 42 | 1119 | 200 | CO-111763 | 1.6 |
| 43 | 1121 | >400 | CO-113747 | 12.5 |
| 44 | 1122 | 400 | CO-111682 | 3.1 |
| 45 | 1123 | >400 | CO-112117 | 6.3 |
| 46 | 1124 | 200 | CO-113739 | 3.1 |
| 47 | 1126 | >400 | CO-113795 | 25 |
| 48 | 1130 | 400 | CO-114139 | 1.6 |
| 49 | 1131 | 400 | CO-114154 | 25 |
| 50 | 1133 | 100 | CO-111629 | 3.1 |
| 51 | MSA 1041 | 100 | MSA 1148 | 3.1 |
| 52 | MSA 1149 | 200 | MSA 1150 | 12.5 |
| 53 | MSA 1152 | 400 | MSA 1159 | 25 |
| 54 | MSA 1155 | 200 | MSA 1171 | 12.5 |
| 55 | MSA 1156 | 100 | MSA 1175 | 6.3 |
| 56 | MSA 1157 | 50 | MSA 1176 | 25 |
| 57 | MSA 1158 | 100 | MSA 1218 | 12.5 |
| 58 | MSA 1160 | 50 | MSA 1223 | 12.5 |
| 59 | MSA 1162 | 400 | MSA 1229 | 25 |
| 60 | MSA 1164 | 50 | MSA 1238 | 0.8 |
| 61 | MSA 1165 | 401 | MSA 1239 | 6.3 |
| 62 | MSA 1172 | 100 | MSA 1240 | 12.5 |
| 63 | MSA 1174 | 100 | MSA 1245 | 12.5 |
| 64 | MSA 1177 | 50 | MSA 1246 | 12.5 |
| 65 | MSA 1221 | 100 | MSA 1248 | 3.1 |
| 66 | MSA 1226 | 200 | MSA 1249 | 25 |
| 67 | MSA 1227 | 200 | MSA 1265 | 12.5 |
| 68 | MSA 1228 | 401 | MSA 2055 | 25 |
| 69 | MSA 1230 | 401 | MSA 4334 | 3.1 |
| 70 | MSA 1231 | 401 | NY 10060906 | 0.8 |
| 71 | MSA 1233 | 401 | NY 10060907 | 12.5 |
| 72 | MSA 1234 | 50 | NY 10070903 | 3.1 |
| 73 | MSA 1235 | 400 | NY 10080904 | 3.1 |
| 74 | MSA 1236 | 200 | NY 10130902 | 12.5 |
| 75 | MSA 1237 | 100 | NY 10140901 | 3.1 |
| 76 | MSA 1241 | 401 | NY 10220905 | 6.3 |
| 77 | MSA 1243 | 401 | NY 11763 | 3.1 |
| 78 | MSA 1244 | 50 | NY 11788 | 25 |
| 79 | MSA 1247 | 100 | NY 11789 | 3.1 |
| 80 | MSA 1250 | 100 | NY 11790 | 3.1 |
| 81 | MSA 1251 | 200 | NY 11900 | 1.6 |
| 82 | MSA 1252 | 400 | NY 12068 | 3.1 |
| 83 | MSA 1253 | 400 | NY 12071 | 0.8 |
| 84 | MSA 1254 | 50 | NY 12102 | 1.6 |
| 85 | MSA 1255 | 400 | NY 12107 | 1.6 |
| 86 | MSA 1256 | 401 | NY 12143 | 12.5 |
| 87 | MSA 1257 | 401 | NY 12144 | 3.1 |
| 88 | MSA 1258 | 400 | NY 12145 | 6.3 |
| 89 | MSA 1259 | 200 | NY 12174 | 6.3 |
| 90 | MSA 1260 | 400 | NY 12182 | 12.5 |
| 91 | MSA 1261 | 400 | NY 12186 | 3.1 |
| 92 | MSA 1262 | 200 | NY 12188 | 25 |
| 93 | MSA 1263 | 200 | NY 12209 | 12.5 |
| 94 | MSA 1264 | 401 | NY 12233 | 3.1 |
| 95 | MSA 1266 | 200 | NY 12260 | 0.8 |
| 96 | MSA 1268 | 100 | NY 12344 | 0.8 |
| 97 | MSA 1269 | 401 | NY 12487 | 1.6 |
| 98 | MSA1154 | 400 | NY 12497 | 0.8 |
| 99 | MSA1232 | 401 | NY 12539 | 1.6 |
| 100 | NY 12498 | 50 | | |
| 101 | NY 3241004 | 50 | | |

TABLE 12

Improved Qualitative Real-time PCR to detect the tvntr6 A238T SNP

Master Mix

| | |
|---|---|
| 2X AccuQuant Custom SuperMix | 7.5 µl |
| ddH$_2$O | 4.0 µl |
| SEQ ID 9 (30 µM) | 0.25 µl |
| SEQ ID 10 (30 µM) | 0.25 µl |
| SEQ ID 11 (10 µM) | 0.5 µl |
| DNA (0.2 µM/ml) | 2.5 µl |
| Total | 15 µl |

Thermal Profile

| Step | Temp | Time |
|---|---|---|
| 1 | 95° C. | 2 min |
| 2 | 95° C. | 15 sec |
| 3 | 63° C. | 45 sec |

*repeat steps 2-3 for 35 cycles
Read using Corbett Research Rotor Gene RG-3000, reading fluorescence on FAM (SEQ ID 11) channel.
Amplification as shown by FAM fluorescence indicates the A238 allele.

TABLE 13

Results of Improved Real-Time PCR Assay to detect tvntr6 A238T SNP in a blind challenge of CDC *Trichomonas vaginalis* isolates.

| | Resistant Isolates | | Sensitive Isolates | | Sensi- | Specif- |
|---|---|---|---|---|---|---|
| SNP | Positive | Negative | Positive | Negative | tivity | icity |
| A238T | 15 | 34 | 2 | 49 | 31 | 96 |

What is claimed is:

1. A kit for detecting metronidazole resistance in *Trichomonas vaginalis* in a human, comprising:
   (a) one or a plurality of reagents for detecting the presence of A238T in tvntr6 in *Trichomonas vaginalis* present in a human, wherein the reagent or plurality of reagents comprises a fluorescently labeled probe consisting of SEQ ID NO: 7; and
   (b) an instruction for use of the reagent or a plurality of reagents in detecting the presence of A238T in trntr6 in *Trichomonas vaginalis*, wherein the presence of A238T in trntr6 in *Trichomonas vaginalis* is indicative metronidazole resistance in *Trichomonas vaginalis*.

2. The kit of claim 1, wherein the plurality of reagents comprises a forward primer consisting of SEQ ID NO 5 and a reverse primer consisting of SEQ ID NO 6.

3. The kit of claim 1, wherein the plurality of reagents comprises a probe consisting of SEQ ID NO: 11, a forward primer consisting of SEQ ID NO: 9 and a reverse primer consisting of SEQ ID NO: 10.

4. The kit of claim 1 further comprising a reagent for isolating nucleic acid.

5. The kit of claim 1 further comprising a reagent for allele-specific PCR and sequencing.

6. The kit of claim 1 further comprising a reagent for PCR and pyrosequencing.

7. The kit of claim 1, wherein the plurality of reagents comprises a fluorescently labeled probe comprising a nucleic acid sequence consisting of SEQ ID NO 11.

* * * * *

SEQUENCE LISTING

<160> NUMBER OF SEQ ID NOS: 21

<210> SEQ ID NO 1
<211> LENGTH: 24
<212> TYPE: DNA
<213> ORGANISM: Homo sapiens

<400> SEQUENCE: 1
atgagtgtcc ttaagtgcat ccaa                                              24

<210> SEQ ID NO 2
<211> LENGTH: 24
<212> TYPE: DNA
<213> ORGANISM: Homo sapiens

<400> SEQUENCE: 2
ttagtcggca taaactacct taga                                              24

<210> SEQ ID NO 3
<211> LENGTH: 24
<212> TYPE: DNA
<213> ORGANISM: Homo sapiens

<400> SEQUENCE: 3
cattgaattt attcgttcaa aatt                                              24

<210> SEQ ID NO 4
<211> LENGTH: 24
<212> TYPE: DNA
<213> ORGANISM: Homo sapiens

<400> SEQUENCE: 4
ttattcaatg tatgtaacct ttct                                              24

<210> SEQ ID NO 5
<211> LENGTH: 24
<212> TYPE: DNA
<213> ORGANISM: Homo sapiens

<400> SEQUENCE: 5
ctccatcagc tatgaatgtt cagg                                              24

<210> SEQ ID NO 6
<211> LENGTH: 24
<212> TYPE: DNA
<213> ORGANISM: Homo sapiens

<400> SEQUENCE: 6
ggaatcaagt tgttgaatgg ctgg                                              24

<210> SEQ ID NO 7
<211> LENGTH: 24
<212> TYPE: DNA
<213> ORGANISM: Homo sapiens

<400> SEQUENCE: 7
tggaatgcaa aagcagacac atgt                                              24

<210> SEQ ID NO 8
<211> LENGTH: 24
<212> TYPE: DNA
<213> ORGANISM: Homo sapiens

<400> SEQUENCE: 8

```
tggaatgcaa tagcagacac atgt                                        24

<210> SEQ ID NO 9
<211> LENGTH: 26
<212> TYPE: DNA
<213> ORGANISM: Homo sapiens

<400> SEQUENCE: 9
cgttgttaca aacaaggaaa aactcc                                      26

<210> SEQ ID NO 10
<211> LENGTH: 20
<212> TYPE: DNA
<213> ORGANISM: Homo sapiens

<400> SEQUENCE: 10
ggatgcacgc tcattcttga                                             20

<210> SEQ ID NO 11
<211> LENGTH: 24
<212> TYPE: DNA
<213> ORGANISM: Homo sapiens

<400> SEQUENCE: 11
tggaatgcaa tagcagacac atgt                                        24

<210> SEQ ID NO 12
<211> LENGTH: 549
<212> TYPE: DNA
<213> ORGANISM: Homo sapiens

<400> SEQUENCE: 12
atgagtgtcc ttaagtgcat ccaagctaga agaacaatta gacactatgt tcagggcgaa    60
gaagttccaa aggcagatat tgatctcatc gcaaacagtg gcttaactgc tccatcttct   120
atggatatcc aaggtgtcga catctacgtc gtcagaggcc aagaaaagct tgccaagatt   180
gaagaagcta cactcaaggc ccttccagaa tacgccacaa agtacttcgt taatcgtcat   240
gaacagcttc atgttaagaa cgttatcacc tgcgatgctc cagttctttt cgtcttagtt   300
aagaatgaga gagctcacaa agattactat catatcgatt gcggtctcat cgtcgaatca   360
atgattttgc ttgcccaaga tatgggatac agcacaatgt gcatcggtgc tatcggtatg   420
gctgatcttt ctgaagttct tggtattcca aaggatgctg ctattatggg tcttgccatg   480
ggtaaagctg ccccagaaca ggatcttcat aaaaggccaa tcaagtctaa ggtagtttat   540
gccgactaa                                                          549

<210> SEQ ID NO 13
<211> LENGTH: 476
<212> TYPE: DNA
<213> ORGANISM: Homo sapiens

<400> SEQUENCE: 13
aagttccaaa ggcacatatt gatctcatcg caaacagtgg cttaactgct ccatcttcta    60
tggatatcca aggtgtcgac atctacgtcg tcagaggcca agaaaagctt gccaagattg   120
aagaagctac actcaaggcc cttccagaat aggccacaaa gtacttcgtt aatcgtcatg   180
aacagcttca tgttaagaac gttatcacct gcgatgctcc agttcttttc gtcttagtta   240
agaatgagag agctcaaaaa gattactatc atatcgattg cggtctcatc gtcgaatcaa   300
```

```
tgattttgct tgcccaagat atgggataca gcacaatgtg catcggtgct atcggtatgg    360
ctgatctttc tgaagttctt ggtattccaa aggatgctgc tattatgggt cttgccatgg    420
gtaaagctgc cccagaacag gatcttcata aaaggccaat caagtctaag gtagtt       476
```

<210> SEQ ID NO 14
<211> LENGTH: 157
<212> TYPE: PRT
<213> ORGANISM: Homo sapiens

<400> SEQUENCE: 14

```
Val Pro Lys Ala His Ile Asp Leu Ile Ala Asn Ser Gly Leu Thr Ala
1               5                   10                  15

Pro Ser Ser Met Asp Ile Gln Gly Val Asp Ile Tyr Val Val Arg Gly
            20                  25                  30

Gln Glu Lys Leu Ala Lys Ile Glu Glu Ala Thr Leu Lys Ala Leu Pro
        35                  40                  45

Glu Ala Thr Lys Tyr Phe Val Asn Arg His Glu Gln Leu His Val Lys
    50                  55                  60

Asn Val Ile Thr Cys Asp Ala Pro Val Leu Phe Val Leu Val Lys Asn
65                  70                  75                  80

Glu Arg Ala Gln Lys Asp Tyr Tyr His Ile Asp Cys Gly Leu Ile Val
                85                  90                  95

Glu Ser Met Ile Leu Leu Ala Gln Asp Met Gly Tyr Ser Thr Met Cys
            100                 105                 110

Ile Gly Ala Ile Gly Met Ala Asp Leu Ser Glu Val Leu Gly Ile Pro
        115                 120                 125

Lys Asp Ala Ala Ile Met Gly Leu Ala Met Gly Lys Ala Ala Pro Glu
    130                 135                 140

Gln Asp Leu His Lys Arg Pro Ile Lys Ser Lys Val Val
145                 150                 155
```

<210> SEQ ID NO 15
<211> LENGTH: 158
<212> TYPE: PRT
<213> ORGANISM: Homo sapiens

<400> SEQUENCE: 15

```
Val Pro Lys Ala Asp Ile Asp Leu Ile Ala Asn Ser Gly Leu Thr Ala
1               5                   10                  15

Pro Ser Ser Met Asp Ile Gln Gly Val Asp Ile Tyr Val Val Arg Gly
            20                  25                  30

Gln Glu Lys Leu Ala Lys Ile Glu Glu Ala Thr Leu Lys Ala Leu Pro
        35                  40                  45

Glu Tyr Ala Thr Lys Tyr Phe Val Asn Arg His Glu Gln Leu His Val
    50                  55                  60

Lys Asn Val Ile Thr Cys Asp Ala Pro Val Leu Phe Val Leu Val Lys
65                  70                  75                  80

Asn Glu Arg Ala His Lys Asp Tyr Tyr His Ile Asp Cys Gly Leu Ile
                85                  90                  95

Val Glu Ser Met Ile Leu Leu Ala Gln Asp Met Gly Tyr Ser Thr Met
            100                 105                 110

Cys Ile Gly Ala Ile Gly Met Ala Asp Leu Ser Glu Val Leu Gly Ile
        115                 120                 125

Pro Lys Asp Ala Ala Ile Met Gly Leu Ala Met Gly Lys Ala Ala Pro
    130                 135                 140
```

Glu Gln Asp Leu His Lys Arg Pro Ile Lys Ser Lys Val Val
145                 150                 155

<210> SEQ ID NO 16
<211> LENGTH: 743
<212> TYPE: DNA
<213> ORGANISM: Homo sapiens

<400> SEQUENCE: 16

```
cattgaattt atttcgttcaa aatttattgc ctgccgaata tctccgcaaa atgaagaaga      60
aggcaatata tgtttatgat aaaaattggg gataaatttt ttgatagtag cctttcaaat     120
ttttgtaaga aaattttgga gaaactgttc ggaaaactaa ttgaaaagaa aaatctcaaa     180
tatgacttca tttttagata atgtctatct cacaactcaa gtccagacgc acaatcagat     240
gctatgatcc aaactatgtc attccaaagg aagacttaga gaaaattgtt gatgcagctt     300
tcaactctcc atcagctatg aatgttcagg aaacagatct cgtcgttgtt acaaacaagg     360
aaaaactcca aaagcttaac gatgctgttt ttgcttccct tgatgagaag tctcaacaaa     420
tgtaccttgg aatgcaaaag cagacacatg ttaagcagga agttctctat gattgctctg     480
ctgttttcct tcttgtcaag aatgagcgtg catcccagc cattcaacaa cttgattccg      540
gtattctcgc catgagtgtt ttgatggctg cccatgatct tggacttggt acggttcctc     600
ttggtacact tatccgccca caaacagaag aagttcttgg tcttccacca aaatcagttc     660
ttcttggcat tggtgttggc aaaccattat ctttcgagcc tcatccaaag gaaaacctta     720
gaaaggttac atacattgaa taa                                             743
```

<210> SEQ ID NO 17
<211> LENGTH: 743
<212> TYPE: DNA
<213> ORGANISM: Homo sapiens

<400> SEQUENCE: 17

```
cattgaattt atttcgttcaa aatttattgc ctgccgaata tctccgcaaa atgaagaaga      60
aggcaatata tgtttatgat aaaaattggg gataaatttt ttgatagtag cctttcaaat     120
ttttgtaaga aaattttgga gaaactgttc ggaaaactaa ttgaaaagaa aaatctcaaa     180
tatgacttca tttttagata atgtctatct cacaactcaa gtccagacgc acaatcagat     240
gctatgatcc aaactatgtc attccaaagg aagacttaga gaaaattgtt gatgcagctt     300
tcaactctcc atcagctatg aatgttcagg aaacagatct cgtcgttgtt acaaacaagg     360
aaaaactcca aaagcttaac gatgctgttt ttgcttccct tgatgagaag tctcaacaaa     420
tgtaccttgg aatgcaaaag cagacacatg ttaagcagga agttctctat gattgctctg     480
ctgttttcct tcttgtcaag aatgagcgtg catcccagc cattcaacaa cttgattccg      540
gtattctcgc catgagtgtt ttgatggctg cccatgatct tggacttggt acggttcctc     600
ttggtacact tatccgccca caaacagaag aagttcttgg tcttccacca aaatcagttc     660
ttcttggcat tggtgttggc aaaccattat ctttcgagcc tcatccaaag gaaaacctta     720
gaaaggttac atacattgaa taa                                             743
```

<210> SEQ ID NO 18
<211> LENGTH: 176
<212> TYPE: PRT
<213> ORGANISM: Homo sapiens

<400> SEQUENCE: 18

Met Ser Ile Ser Gln Leu Lys Ser Arg Arg Thr Ile Arg Cys Tyr Asp
1               5                   10                  15

Pro Asn Tyr Val Ile Pro Lys Glu Asp Leu Glu Lys Ile Val Asp Ala
                20                  25                  30

Ala Phe Asn Ser Pro Ser Ala Met Asn Val Gln Glu Thr Asp Leu Val
            35                  40                  45

Val Val Thr Asn Lys Glu Lys Leu Gln Lys Leu Asn Asp Ala Val Phe
    50                  55                  60

Ala Ser Leu Asp Glu Lys Ser Gln Gln Met Tyr Leu Gly Met Gln Gln
65                  70                  75                  80

Thr His Val Lys Gln Glu Val Leu Tyr Asp Cys Ser Ala Val Phe Leu
                85                  90                  95

Leu Val Lys Asn Glu Arg Ala Ser Pro Ala Ile Gln Gln Leu Asp Ser
                100                 105                 110

Gly Ile Leu Ala Met Ser Val Leu Met Ala Ala His Asp Leu Gly Leu
            115                 120                 125

Gly Thr Val Pro Leu Gly Thr Leu Ile Arg Pro Gln Thr Gln Glu Val
    130                 135                 140

Leu Gly Leu Pro Pro Lys Ser Val Leu Leu Gly Ile Gly Ala Gly Lys
145                 150                 155                 160

Pro Leu Ser Phe Glu Pro His Pro Lys Glu Asn Leu Arg Lys Val Thr
                165                 170                 175

<210> SEQ ID NO 19
<211> LENGTH: 177
<212> TYPE: PRT
<213> ORGANISM: Homo sapiens

<400> SEQUENCE: 19

Met Ser Ile Ser Gln Leu Lys Ser Arg Arg Thr Ile Arg Cys Tyr Asp
1               5                   10                  15

Pro Asn Tyr Val Ile Pro Lys Glu Asp Leu Glu Lys Ile Val Asp Ala
                20                  25                  30

Ala Phe Asn Ser Pro Ser Ala Met Asn Val Gln Glu Thr Asp Leu Val
            35                  40                  45

Val Val Thr Asn Lys Glu Lys Leu Gln Lys Leu Asn Asp Ala Val Phe
    50                  55                  60

Ala Ser Leu Asp Glu Lys Ser Gln Gln Met Tyr Leu Gly Met Gln Lys
65                  70                  75                  80

Gln Thr His Val Lys Gln Glu Val Leu Tyr Asp Cys Ser Ala Val Phe
                85                  90                  95

Leu Leu Val Lys Asn Glu Arg Ala Ser Pro Ala Ile Gln Gln Leu Asp
                100                 105                 110

Ser Gly Ile Leu Ala Met Ser Val Leu Met Ala Ala His Asp Leu Gly
            115                 120                 125

Leu Gly Thr Val Pro Leu Gly Thr Leu Ile Arg Pro Gln Thr Glu Glu
    130                 135                 140

Val Leu Gly Leu Pro Pro Lys Ser Val Leu Leu Gly Ile Gly Val Gly
145                 150                 155                 160

Lys Pro Leu Ser Phe Glu Pro His Pro Lys Glu Asn Leu Arg Lys Val
                165                 170                 175

Thr

<210> SEQ ID NO 20
<211> LENGTH: 155

```
<212> TYPE: PRT
<213> ORGANISM: Homo sapiens

<400> SEQUENCE: 20

Val Pro Lys Ala Ile Asp Leu Ile Ala Asn Ser Gly Leu Thr Ala Pro
1               5                   10                  15

Ser Ser Met Asp Ile Gln Gly Val Asp Ile Tyr Val Val Arg Gly Gln
            20                  25                  30

Glu Lys Leu Ala Lys Ile Glu Glu Ala Thr Leu Lys Ala Leu Pro Glu
        35                  40                  45

Ala Thr Lys Tyr Phe Val Asn Arg His Glu Gln Leu His Val Lys Asn
    50                  55                  60

Val Ile Thr Cys Asp Ala Pro Val Leu Phe Val Leu Val Lys Asn Glu
65                  70                  75                  80

Arg Ala Lys Asp Tyr Tyr His Ile Asp Cys Gly Leu Ile Val Glu Ser
                85                  90                  95

Met Ile Leu Leu Ala Gln Asp Met Gly Tyr Ser Thr Met Cys Ile Gly
            100                 105                 110

Ala Ile Gly Met Ala Asp Leu Ser Glu Val Leu Gly Ile Pro Lys Asp
        115                 120                 125

Ala Ala Ile Met Gly Leu Ala Met Gly Lys Ala Ala Pro Glu Gln Asp
    130                 135                 140

Leu His Lys Arg Pro Ile Lys Ser Lys Val Val
145                 150                 155

<210> SEQ ID NO 21
<211> LENGTH: 174
<212> TYPE: PRT
<213> ORGANISM: Homo sapiens

<400> SEQUENCE: 21

Met Ser Ile Ser Gln Leu Lys Ser Arg Arg Thr Ile Arg Cys Tyr Asp
1               5                   10                  15

Pro Asn Tyr Val Ile Pro Lys Glu Asp Leu Glu Lys Ile Val Asp Ala
            20                  25                  30

Ala Phe Asn Ser Pro Ser Ala Met Asn Val Gln Glu Thr Asp Leu Val
        35                  40                  45

Val Val Thr Asn Lys Glu Lys Leu Gln Lys Leu Asn Asp Ala Val Phe
    50                  55                  60

Ala Ser Leu Asp Glu Lys Ser Gln Gln Met Tyr Leu Gly Met Gln Gln
65                  70                  75                  80

Thr His Val Lys Gln Glu Val Leu Tyr Asp Cys Ser Ala Val Phe Leu
                85                  90                  95

Leu Val Lys Asn Glu Arg Ala Ser Pro Ala Ile Gln Gln Leu Asp Ser
            100                 105                 110

Gly Ile Leu Ala Met Ser Val Leu Met Ala Ala His Asp Leu Gly Leu
        115                 120                 125

Gly Thr Val Pro Leu Gly Thr Leu Ile Arg Pro Gln Thr Glu Val Leu
    130                 135                 140

Gly Leu Pro Pro Lys Ser Val Leu Leu Gly Ile Gly Gly Lys Pro Leu
145                 150                 155                 160

Ser Phe Glu Pro His Pro Lys Glu Asn Leu Arg Lys Val Thr
                165                 170
```